US010582286B2

(12) United States Patent
Eddins et al.

(10) Patent No.: US 10,582,286 B2
(45) Date of Patent: Mar. 3, 2020

(54) METHOD FOR TREATING DEBILITATING HYPERACUSIS

(71) Applicants: David Alan Eddins, Odessa, FL (US); Charles Craig Formby, Essex, MD (US); Stephen W. Armstrong, Burlington (CA)

(72) Inventors: David Alan Eddins, Odessa, FL (US); Charles Craig Formby, Essex, MD (US); Stephen W. Armstrong, Burlington (CA)

(73) Assignees: University of South Florida, Tampa, FL (US); The Board of Trustees of the University of Alabama, Tuscaloosa, AL (US); SoundsGood Labs, Inc. (CA)

( * ) Notice: Subject to any disclaimer, the term of this patent is extended or adjusted under 35 U.S.C. 154(b) by 0 days.

(21) Appl. No.: 16/450,023

(22) Filed: Jun. 24, 2019

(65) Prior Publication Data

US 2019/0394551 A1   Dec. 26, 2019

Related U.S. Application Data

(60) Provisional application No. 62/688,492, filed on Jun. 22, 2018.

(51) Int. Cl.
*H04R 25/00* (2006.01)
*H04R 1/10* (2006.01)
*A61F 11/08* (2006.01)

(52) U.S. Cl.
CPC ............ *H04R 1/1016* (2013.01); *A61F 11/08* (2013.01); *H04R 25/505* (2013.01); *H04R 25/75* (2013.01); *H04R 25/502* (2013.01); *H04R 25/558* (2013.01); *H04R 2420/07* (2013.01)

(58) Field of Classification Search
CPC ........ A61F 11/08; A61F 11/00; H04R 1/1016; H04R 2420/07; H04R 25/00; H04R 25/502; H04R 25/505; H04R 25/558; H04R 25/75; H04R 1/10; A61B 5/00; A61M 21/00; G06K 9/00; A61H 23/00; A61N 1/36
USPC .......... 128/864; 381/60, 309, 312, 328, 329, 381/330, 73.1, 104, 314, 317, 320, 322,
(Continued)

(56) References Cited

U.S. PATENT DOCUMENTS 5,628,330 A * 5/1997 Upham .................. A61F 11/00
128/864
6,048,305 A * 4/2000 Bauman .................. H04R 3/00
600/25
(Continued)

OTHER PUBLICATIONS

Cox, R. M., et al., (1997). The contour test of loudness perception. Ear and Hearing. 18, 388-400.
(Continued)

*Primary Examiner* — Gerald Gauthier
(74) *Attorney, Agent, or Firm* — Michele L. Lawson; Smith & Hopen, P.A.

(57) ABSTRACT

A system and method of treating hyperacusis is presented. The system uses a customizable, patient-specific, in-ear device combining sound attenuation with loudness suppression and a noise generator to expand the dynamic range of a patient. This device is used with novel software and counseling to provide a patient-specific treatment to hypersensitivity to sound.

20 Claims, 18 Drawing Sheets

(58) Field of Classification Search
USPC ......... 381/72; 600/25, 26, 28, 559; 704/502; 601/47; 607/3
See application file for complete search history.

(56) References Cited

U.S. PATENT DOCUMENTS

| | | | | |
|---|---|---|---|---|
| 6,394,947 | B1* | 5/2002 | Leysieffer | H04R 25/505 600/25 |
| 6,682,472 | B1* | 1/2004 | Davis | A61B 5/121 600/25 |
| 7,520,851 | B2* | 4/2009 | Davis | A61B 5/121 600/25 |
| 8,218,799 | B2* | 7/2012 | Murphy | H04R 1/1016 381/309 |
| 8,503,703 | B2* | 8/2013 | Eaton | H04R 25/554 381/312 |
| 9,913,053 | B2* | 3/2018 | Jensen | H04R 25/75 |
| 10,165,372 | B2* | 12/2018 | Dyrlund | H04R 25/75 |
| 2004/0047482 | A1* | 3/2004 | Bauman | H04R 25/604 381/322 |
| 2004/0047483 | A1* | 3/2004 | Bauman | H04R 25/604 381/330 |
| 2004/0141624 | A1* | 7/2004 | Davis | A61B 5/121 381/73.1 |
| 2006/0167335 | A1* | 7/2006 | Park | A61F 11/00 600/25 |
| 2007/0127755 | A1* | 6/2007 | Bauman | H04R 25/00 381/328 |
| 2007/0133832 | A1* | 6/2007 | DiGiovanni | H04R 25/552 381/320 |
| 2008/0205660 | A1* | 8/2008 | Goldstein | A61B 5/0002 381/60 |
| 2011/0040205 | A1* | 2/2011 | Parra | A61B 5/121 600/559 |
| 2011/0071340 | A1* | 3/2011 | McGuire | A61M 21/00 600/28 |
| 2011/0105967 | A1* | 5/2011 | Zeng | A61M 21/00 601/47 |
| 2012/0283593 | A1* | 11/2012 | Searchfield | H04R 25/75 600/559 |
| 2012/0308060 | A1* | 12/2012 | Pontoppidan | H04R 25/505 381/317 |
| 2013/0039517 | A1* | 2/2013 | Nielsen | H04R 25/75 381/314 |
| 2013/0072996 | A1* | 3/2013 | Kilgard | A61N 1/36036 607/3 |
| 2013/0163797 | A1* | 6/2013 | Suzman | H04R 25/50 381/314 |
| 2013/0336508 | A1* | 12/2013 | Galster | H04R 25/48 381/314 |
| 2014/0275737 | A1* | 9/2014 | Shore | A61M 21/02 600/26 |
| 2014/0363007 | A1* | 12/2014 | DiGiovanni | H04R 25/75 381/60 |
| 2015/0003635 | A1* | 1/2015 | Baker | H03G 3/00 381/104 |
| 2015/0005661 | A1* | 1/2015 | Trammell | H04R 25/75 600/559 |
| 2015/0120310 | A1* | 4/2015 | Roberts | H04R 25/70 704/502 |
| 2016/0030245 | A1* | 2/2016 | Perry | H04R 25/75 600/28 |
| 2016/0249145 | A1* | 8/2016 | Ohl | H03G 3/3026 |
| 2016/0255449 | A1* | 9/2016 | Bauman | G10K 11/16 381/329 |
| 2016/0366527 | A1* | 12/2016 | Jones | A61M 21/00 |
| 2017/0071534 | A1* | 3/2017 | Zhao | G16H 40/67 |
| 2017/0171677 | A1* | 6/2017 | Norris | H04R 25/75 |
| 2017/0347213 | A1* | 11/2017 | Goorevich | H04R 25/356 |
| 2017/0353807 | A1* | 12/2017 | Lim | H04R 25/75 |
| 2018/0035216 | A1* | 2/2018 | Van Hasselt | H04R 25/505 |
| 2018/0262854 | A1* | 9/2018 | Arnold | H04R 25/75 |
| 2018/0271710 | A1* | 9/2018 | Boesen | A61M 21/00 |
| 2018/0288540 | A1* | 10/2018 | Micheyl | H04R 25/70 |
| 2019/0163952 | A1* | 5/2019 | Mueller-Wehlau | G06K 9/0053 |
| 2019/0201657 | A1* | 7/2019 | Popelka | A61B 5/128 |
| 2019/0261105 | A1* | 8/2019 | Ohl | H03G 3/02 |
| 2019/0344073 | A1* | 11/2019 | Baker | A61N 1/361 |
| 2019/0394551 | A1* | 12/2019 | Eddins | A61F 11/08 |

OTHER PUBLICATIONS

Formby, C. et al., Repeated Measurement of Absolute and Relative Judgments of Loudness: Clinical Relevance for Prescriptive Fitting of Aided Target Gains for soft, Comfortable, and Loud, But Ok Sound Levels, Seminar in Hearing, Feb. 2017;38(1):26-52.

Formby, C. and Gold, S., Modification of loudness discomfort level: Evidence for adaptive chronic auditory gain and its clinical relevance, Seminars in Hearing, 2002, 23(1):21-34.

Formby, C., and Keaser, M.L., (2007). Secondary Treatment Benefits Achieved by Hearing-Impaired Tinnitus Patients Using aided Environmental Sound Therapy for Tinnitus Retraining Therapy: Comparisons with Matched Groups of Tinnitus Patients Using Noise Generators for Sound Therapy. Seminars in Hearing. 28(4), 276-294.

Formby, C., Gold, S.L., Keaser, M.L., Block, K.L., and Hawley, M.L. (2007). Secondary benefits from Tinnitus Retraining Therapy (TRT): Clinically significant increases in loudness discomfort level and in the auditory dynamic range. Seminars in Hearing. 28(4), 276-294.

Formby C., et al., A sound therapy-based intervention to expand the auditory dynamic range for loudness among persons with sensorineural hearing losses: a randomized placebo-controlled clinical trial, Seminars in Hearing, 2015, 26(2):77-109.

Sherlock, L and Formby, C., Estimates of loudness, loudness discomfort, and the auditory dynamic range: normative estimates, comparison of procedures, and test-retest reliability, J. Am. Acad. Audiol., 2005, 16(2):85-100.

Jastreboff, P. J., and Jastreboff, M. M., (2000). Tinnitus retraining therapy (TRT) as a method for treatment of tinnitus and hyperacusis patients. Journal of American Academy of Audiology. 11, 162-177.

Goldstein, B. And Schulman, A., Tinnitis—hyperacusis and the loudness discomfort level test—a preliminary report, International Tinnitis Journal, 1996, 2:83-89.

Tyler, R. S., et al., (2014). A review of hyperacusis and future directions: Part I. definitions and manifestations. American Journal of Audiology. 23, 401-419.

Andersson, G., et al., (2002). Hypersensitivity to sound (hyperacusis):A prevalence study conducted via the Internet and post. International Journal of Audiology. 41, 545-554.

Sammeth, C. et al., Hyperacusis: Case studies and evaluation of electronic loudness suppression devices as a treatment approach, Scand. Audiology, 2000, 29:28-36.

Pienkowski, M., et al., (2014). A review of hyperacusis and future directions: Part II, measurement, mechanisms, and treatment. American Journal of Audiology. 23, 420-436.

Scherer, R.W., et al. Tinnitus Retraining Therapy Trial Research Group. The Tinnitus Retraining Therapy Trial (TRTT): study protocol for a randomized controlled trial. Trials. Oct. 15, 2014;15:396.

Hazell, J. W. P., et al., (2002). Decreased sound tolerance: predisposing factors, triggers, and outcomes after TRT. In Patuzzi R. (Ed), Proceedings of the Seventh International Tinnitus Seminar. Crawley, W. A., Australia: University of Western Australia, pp. 255-261.

Hamilton, A. M., and Munro, K. J., (2010). Uncomfortable loudness levels in experienced unilateral and bilateral hearing aid users: Evidence of adaptive plasticity following asymmetrical sensory input. International Journal of Audiology. 49, 667-671.

Formby, C., and Scherer, R. TRTT Study Group; Rationale for the tinnitus retraining therapy trial. Noise Health. Mar.-Apr. 2013; 15(63): 134-42.

Jastreboff, P.J., and Jastreboff, M.M., (2014). Treatments for decreased sound tolerance (hyperacusis and misophonia). Seminars in Hearing. 35, 10-120.

(56) References Cited

OTHER PUBLICATIONS

Formby, C., et al., (2007). Adaptive recalibration of chronic auditory gain. Seminars in Hearing. 28(4), 295-302.
Formby, C. And Gold, S., Structured counseling for auditory dynamic range expansion, Seminars in Hearing, 2017, 38 (1):115-129.
McKinney, C. J., et al., (1999). Changes in loudness discomfort level and sensitivity to environmental sound with habituation based therapy. In Hazell, J.W.P. (Ed.), Proceedings of the Sixth International Tinnitus Seminar. London, UK: The Tinnitus and Hyperacusis Centre, pp. 499-501.
Schmitz, H.D., (1969). Loudness discomfort level modification. J. Speech Hear. Res., vol. 12: 807-817.
Wolk, C., and Seefeld, B., (1999). The effects of managing hyperacusis with maskers (noise generators). In Hazell, J.W.P. (Ed.) Proceedings of the Sixth International Tinnitus Seminar, London; England: The Tinnitus and Hyperacusis Centre, pp. 512-514.
Dauman, R., and Bouscau-Faure, F. (2005). Assessment and amelioration of hyperacusis in tinnitus patients. Acta Oto-Laryngologica. 125, 503-509.
Formby, C., et al., (2008). Intervention for restricted dynamic range and reduced sound tolerance. Proceedings of Meetings on Acoustics, The Acoustical Society of America, Acoustics '08 Paris, www.acoustics08-paris.org, pp. 4705-4709.
Formby, C. et al., Adaptive plasticity of loudness induced by chronic attenuation and enhancement of the acoustic background, J. Acoust. Soc. Am., Jul. 2003, 114(1):55-58.
Formby, C., et al., (2013). Intervention for restricted dynamic range and reduced sound tolerance: Clinical trial using a Tinnitus Retraining Therapy protocol for hyperacusis. Proceedings of the 21st International Congress on Acoustics, Proceedings of Meetings on Acoustics. 19(050083):1-5.
Gold, S., et al., (1999). Shifts in dynamic range for hyperacusis patients receiving tinnitus retraining therapy (TRT). In Hazell, J.W.P. (Ed.), Proceedings of the 6th International Tinnitus Seminar. London: The Tinnitus and Hyperacusis Centre, 297-301.
Juris, L, et al., (2013). The Hyperacusis Questionnaire, loudness discomfort levels, and the Hospital Anxiety and Depression Scale: A cross-sectional study, Hearing, Balance and Communication, 11:2, 72-79, DOI: 10.3109/21695717.2013.780409 to link.
Silverman, S.R., (1947). Tolerance for Pure Tones and Speech in Normal and Defective Hearing. Annals of Otology, Rhinology and Laryngology; vol. 56, 658-677.
Jastreboff, Pawel J. And Jonathan W.P. Hazell. A neurophysiological approach to tinnitus: clinical implications. British Journal of Audiology, 1993, 27, 7-17.
Sandlin, Robert E. and Robert J. Olsson. Evaluation and Selection of Maskers and Other Devices Used in the Treatment of Tinnitus and Hyperacusis. Trends in Amplification, vol. 4, No. 1, 1999, 6-26.
Souza, Pamela E et al. Measuring the acoustic effects of compression amplification on speech in noise (L). J. Acoust. Soc. Am. 119(1), Jan. 2006, 41-44.

Alexander, Joshua M. and Katie Masterson. Ear Hear, 2015; 36(2): e35-e49. doi: 10.1097/AUD.0000000000000115.
Formby et al. Intervention for restricted dynamic range and reduced sound tolerance: clinical trial using a tinnitus retraining therapy protocol for hyperacusis. J. Acoust. Soc. Am., vol. 133, No. 5, Pt. 2, May 2013, 3382.
Bartnik, Grazyna et al. Distortion Product Otoacoustic Emission Levels and Input/Output-Growth Functions in Normal-Hearing Individuals with Tinnitus and/or Hyperacusis. Seminars in Hearing. Hyperacusis and Related Sound Tolerance Complaints: Differential Diagnosis, Treatment Effects, and Models, Nov. 2007; vol. 28, No. 4, pp. 303-318.
Formby, Craig et al. A Sound Therapy-Based Intervention to Expand the Auditory Dynamic Range for Loudness among Persons with Sensorineural Hearing Losses: A Randomized Placebo-Controlled Clinical Trial. Semin Hear. May 2015; 36(2): 77-110.
Gold, S.L., et al. Incremental shifts in loudness discomfort level among tinnitus patients with and without hyperacusis. In Patuzzi, R. (Ed.), Proceedings of the 7th International Tinnitus Seminar. Crawley, W.A., Australia, Univ. Western Australia, (2002) pp. 170-173.
Gold, S.L., et al., (2002). Shifts in dynamic range for hyperacusis patients receiving tinnitus retraining therapy (TRT). In Patuzzi R. (Ed), Proceedings of the 6th International Tinnitus Seminar. Cambridge, UK, British Society of Audiology,, pp. 297-301.
Jastrehoff, PJ et al. Audiometrical characterization of hypercusis patients before and during TRT. Proceedings of the 6th International Tinnitus Seminar, Cambridge, UK, British Society of Audiology, pp. 495-498.
Formby, Craig, et al. (2007). Secondary Benefits from Tinnitus Retraining Therapy: Clinically Significant Increases in Loudness Discomfort Level and Expansion of Auditory Dynamic Range. Seminars in Hearing. 28(4), 227-260.
Formby, Craig, et al. (2007). Adaptive Recalibration of Chronic Auditory Gain. Seminars in Hearing. 28(4), 295-302.
Hazell, J.W.P. and Sheldrake, J.B., Proceedings of the Fourth International Tinnitus Seminar, Bordeaux, France, Aug. 27-30, 1991, Kugler Publications, Amsterdam/New York, 1992; pp. 245-248.
Hawley, Monica L. and Keaser, Michael L. Predicting Hyperacusis in Tinnitus Patients. Seminars in Hearing. Hyperacusis and Related Sound Tolerance Complaints: Differential Diagnosis, Treatment Effects, and Models, Nov. 2007; vol. 28, No. 4, pp. 261-275.
Formby, Craig and Keaser, Michael L. Secondary Treatment Benefits Achieved by Hearing-Impaired Tinnitus Patients Using Aided Environmental Sound Therapy for Tinnitus Retraining Therapy: Comparisons with Matched Groups of Tinnitus Patients Using Noise Generators for Sound Therapy. Seminars in Hearing, Nov. 2007. vol. 28, No. 4, pp. 276-294.
Hazell, Jonathan. Proceedings of the Sixth International Tinnitus Seminar hosted by the British Society of Audiology in Cambridge UK, Sep. 5-9, 1999.

* cited by examiner

Normal-Gain System

Loudness Hyperacusis Modeled as a Hyper-Gain System

Hyper-Gain System with Emotional Associations and Physiological Responses

Hyper-Gain System with Emotional Associations and Habitation of Physiological Responses

Hyper-Gain System and Habitation of Emotional Associations and Physiological Responses

Normal-Gain System following Recalibration of Gain and Habituation of Emotional Associations and Physiological Responses

| Classification of Hyperacusis | | |
|---|---|---|
| Hyperacusis | Dynamic Range | Loudness Discomfort Level* |
| None/Negative | 60 dB or greater all frequencies | 95 dB or greater all frequencies |
| Mild | 50-55 dB at any frequency | 80-90 dB at 2 or more frequencies |
| Moderate | 40-45 dB at any frequency | 65-75 dB at 2 or more frequencies |
| Severe | 35 dB or less at any frequency | 60 dB or lower at 2 or more frequencies |

* Loudess Hyperacusis

FIG. 21A-D

METHOD FOR TREATING DEBILITATING HYPERACUSIS

CROSS REFERENCE TO RELATED APPLICATIONS

This application is a nonprovisional of and claims priority to U.S. Provisional Patent Application Ser. No. 62/688,492, entitled "Method for Treating Debilitating Hyperacusis", filed Jun. 22, 2018, the contents of which are hereby incorporated by reference into this disclosure.

GOVERNMENT INTEREST

This invention was made with Government support under Grant Nos. R21 DC015054 and R01 DC018328 awarded by the National Institutes of Health. The Government has certain rights in the invention.

FIELD OF INVENTION

This invention relates to treatment of hyperacusis. Specifically, the invention provides a method of treatment of hyperacusis using a novel behind-the-ear device and counseling protocol.

BACKGROUND OF THE INVENTION

Hyperacusis is an unusual intolerance to the loudness of an ordinary environment. Patients suffering from hyperacusis have an abnormally strong reaction to sounds within the auditory system that is manifested by inordinate discomfort to sound that would not evoke a similar reaction in the average listener. The estimated prevalence of hyperacusis in the general population is between about 0.6% and 15%. About 85%-90% of hyperacusis patients have an associated tinnitus condition. (Anari et al. 1999; Nelting 2002). It has been reported that up to about 55% of patients with tinnitus also have hyperacusis. (Schecklmann et al. 2014).

In some cases, patients suffering from hyperacusis exhibit symptoms of phonophobia which is a specific type of phobia in which the individual has a persistent, abnormal and unwarranted fear of sound. The resulting hypervigilance accounts for the exaggerated behavior in a patient's awareness to the sound environment.

Patients having hyperacusis may also exhibit symptoms of misophonia in which the individual experiences a strong, unpleasant reaction to ordinary sounds. This selective sensitivity to specific sounds may be accompanied by emotional distress and behavioral responses such as avoidance. In some instances, patients may also have pain associated with the hyperacusis. Neither hyperacusis, misophonia nor phonophobia have any relation to hearing thresholds. In hyperacusis, the auditory system is not working poorly but rather, it is working too well and overcompensating to a change in the normal gain setting of the auditory system.

Hyperacusis is associated with several peripheral and central auditory diseases as well as many non-auditory diseases. Exemplary disorders exhibiting hyperacusis symptoms include otosclerosis; efferent dysfunction; TMJ dysfunction; Bell's palsy; Meniere's disease; perilymphatic fistula; acute acoustic trauma; Lyme disease; autism; traumatic head injury; migraines; depression; childhood learning disability; diminished serotonin function; central auditory pathway lesions; William's syndrome; intracranial hypotension; myasthenia gravis; and Ramsey Hunt syndrome.

The auditory system is comprised of the outer ear, the middle ear and the inner ear as shown in FIG. 1. The outer ear is comprised of the pinna, the structure visible from the outside. It captures and directs sound waves into the ear canal, which in turn cause mechanical vibration of the eardrum. Behind the eardrum is the middle ear, which is an air-filled space that has a chain of 3 interconnected small bones. A sound wave vibrates the eardrum which vibrates the three bones. The third bone moves like a piston in and out of a membranous window at the entrance to the inner ear. The outer and middle ear facilitate sound transmission to the inner ear. The inner ear has 2 primary components: the balance system and the cochlea. The balance system has 3 semicircular canals that have nerve endings which send spatial information to the brain to balance and associate the body's position in space. The cochlea is the sensory organ for hearing. The cochlea is a hollow tube filled with fluid that spirals around and a membrane that has hair cells positioned on and spiraling around the tube. A hair cell has 3 parts: a main body (largest part), cilia at the top that are the tiny little hair fibers atop the main body and a connection to the nerve. Cilia can be thought of as mini hair cells that move back and forth when there's fluid motion inside the cochlea. When we hear a sound, there is movement of the fluid, bending of the membrane supporting the main hair cells, and bending of the cilia back and forth. This movement activates the big hair cells to send the auditory electrical signal via the nerve fibers to the brain. The hair cells transform mechanical energy (fluid motion) into an electrochemical signal so that the brain can process it.

There are two types of HCs: inner hair cells (IHCs) and outer hair cells (OHCs). IHCs are the primary sensory transducers of sound with 95% of the connecting neural fibers carrying auditory signals from the cochlea to the brain, where the signal is recognized as sound. Neural activity from IHCs go in one direction and receive little or no input back from the brain. The IHCs are sheltered and protected from damage more than the OHCs, which have a different function. The OHCs boost the strength of the auditory signal and fine tune it. The OHCs have the ability to amplify sounds instantaneously, up to 60 dB, to help the IHCs boost sounds if someone is talking softly or to attenuate sounds if they are loud. If the patient has hearing loss affecting the OHCs then this amplifying and fine tuning mechanism is diminished. OHCs send signals or impulses along the nerve fibers going up to the brain, but, unlike the IHCs, they have large numbers of nerve fibers coming from the brain back to the OHCs thus OHCs have control from the brain. This unique innervation characteristic suggests that the OHCs contribute to the instantaneous gain adjustment to sound, but the primary gain mechanism giving rise to hyperacusis is likely at the higher central level of the auditory system, above the cochlea. OHCS are very vulnerable to damage from noise, ototoxic drugs, viral infections and aging. Fortunately, OHCs are abundant; it has been estimated that humans could lose up to 30% of OHCs, spread evenly throughout the cochlea and still have normal puretone hearing thresholds.

The basilar membrane is frequency specific, meaning that different frequencies stimulate the cochlea at different locations. With regard to cochlear structure, the high frequency (HF) hair cells are located at the entrance of the cochlea where neural fibers are stimulated, and low frequency (LF) structures are stimulated and located distally to the entrance. The hair cells that respond to the higher frequencies, at the entrance to the cochlea, are more vulnerable to wear and tear which is why high frequency hearing loss is experienced more than low frequency hearing loss.

The nerve fibers in the auditory pathways cross over to stimulate both sides of the brain. This neural crossover from both ears facilitates localization of sound. This brings us up to the cortex, the cognitive center of the brain, where auditory signals are interpreted as sound. FIG. 2 highlights the complex auditory neural pathways arising from the cochlea, carrying auditory signals to the auditory cortex. This is the ascending pathway. There is an equally complex descending pathway from the auditory cortex back to the cochlea that is not shown here. The complex interactions between these two pathways control the gain of the auditory system.

There are 5 subcortical, lower levels within the central auditory pathways leading to the cortical brain that are responsible for filtering and enhancing information from the periphery. Each person weighs and processes information differently at these lower subcortical levels which also contribute to the central auditory gain.

These lower level structures work in different ways to affect the perception of sounds. One way is through selective perception in which the brain determines what is normal and filters out extraneous information that does not need attention such as refrigerator noise, the feel of our clothes, etc. The brain also processes information through sensory contrast in which the signal is examined in relation to its background. For example, a candle in dark room shines more brightly than in a sunny room. A third way the brain processes information is by prioritizing information and tasks in which the perceived importance of the signal is prioritized over the strength of the signal. Once the brain determines that the sound is not a threat and there is no danger, then it can override the information provided by the sound signal which permits the brain to intervene to change the perception of sounds. In the hyperacusis patient, the patient's system is too sensitive to all sounds, so it is unable to prioritize the specific important sounds. Perception happens in the cortical area, the primary auditory cortex, after processing the information from the subcortical areas.

The primary central gain mechanism presumably reflects processing in the subcortical areas. An example of the representation of "gain" is a dial that is normally set to 0. When the dial is turned clockwise there is an increase in central auditory gain, giving rise to the perception of a louder signal which is manifested by decreased LDLs consistent with hyperacusis. However, when the dial is turning back toward 0, the LDLs increase as the auditory gain is reduced and the signal is perceived to be less loud, which in turn results in expansion of the dynamic range. There is a constant low level of activity happening within the auditory pathways at all times. When everything is silent within the listening environment, there is an ongoing low level of neuronal activity. In hyperacusis, there is a form of neural hyperactivity ongoing. Gain is being adjusted (increased or decreased) in the subcortical areas. More specifically, some research suggests that the inferior colliculus has an important role in gain adjustment because this is where auditory information is first integrated by the two ears. Primary hyperacusis is almost always, if not solely, a bilateral problem and therefore an auditory pathway problem. The problem arises from abnormally elevated gain within the auditory pathways, which is represented by the reduced LDLs and reduced tolerance to sounds. Thus, whatever the cause or trigger of hyperacusis has resulted in increased auditory gain. If a patient wears earplugs to prohibit sound from coming into the system, the brain realizes that there is reduced or zero input and in response increases the gain of the system. This additional increase in the gain further exacerbates hyperacusis, resulting in even lower LDLs. When the system increases the gain, sounds are perceived louder than they were prior to use of sound-attenuating ear protection which is the reason earplugs are not effective as a treatment for hyperacusis.

In a normal-gain system, sound is transmitted to the peripheral ear (cochlea and nerve). (FIG. 3). As stated above, five subcortical areas of the brain process sound from the periphery of the ear and contribute to the gain system. Auditory activity is detected and filtered at the subcortical levels. If a signal is determined to be a neutral stimulus, these areas of the brain filter out the signal and send other important sounds to the auditory cortex with a normal gain, i.e. using the example enumerated above, the dial remains at 0. The auditory cortex then processes the subcortical information and the signal is perceived as sound.

In a hyper-gain system, sound is transmitted to the peripheral ear (cochlea and nerve) as in the normal-gain system. (FIG. 4). In the normal-gain system, neuronal processes in the auditory subcortical areas are operating in a state of equilibrium in terms of their excitatory and inhibitory actions. Abnormal changes in either set of actions can give rise to increased central auditory gain and hyperacusis. Moreover, if the subcortical areas view the signal as different, dangerous or new, then the subcortical processing enhances the associated neuronal activity, i.e. the dial registers this increase as a change in the gain setting. If the mechanisms that control auditory system gain abnormally amplify a signal, then the result is the perception of an abnormally loud sound in the auditory cortex thus resulting in primary hyperacusis.

There is no universal treatment for or proven cure for hyperacusis. Traditional treatments for hyperacusis include counseling such as hyperacusis activities treatment, social support and cognitive behavioral therapy or sound therapies such as sound attenuation and medication. (Pienkowski et al. 2014). The main goal of sound therapy is to expand the upper end of the dynamic range. Use of low-level broadband sound may be used to enhance sound tolerance. Although the underlying mechanisms are not now known, virtually all treatments using sound-enriching therapy implicitly or explicitly assume a recalibration or desensitization process by which controlled sound exposure gradually resets abnormally high auditory-pathway gain through an adaptive and plastic homeostatic neuronal process. Hazell and Sheldrake experimented with sound therapy using noise generators and increased LDLs in patients 8 to 10 dB over 2 to 6 months with 53% of patients showing treatment effects within 2 months and 73% of patients showing treatment effects within 6 months. The protocol was adopted into tinnitus retraining therapy (TRT). (Hazell & Sheldrake 1992).

In contrast, it has been found that hearing aids do not induce LDL changes. In analyzing the University of Maryland Tinnitus & Hyperacusis Clinic (UMTHC) records, it was found that the LDL change averaged 2.7 dB for 25 aided tinnitus patients with SNHL while matched groups who used noise generators for sound therapy showed changes from 5.9 to 10.1 dB. It was shown that patients with TRT+aided environmental sound have smaller LDL change than patients using noise generators for their sound therapy. In addition, patients using noise generators exhibited subjective improvements in sound tolerance and showed positive treatment effects regardless of the presence or absence of hearing loss, tinnitus and/or hyperacusis. (Formby et al. 2007).

Formby et al. examined the effect of counseling on patients having bilateral hearing loss with and without use of noise generators in a randomized, placebo-controlled study. It was found that treatment that included both counseling as well as noise generators was more efficacious than either treatment alone. (Formby et al. 2015)

Sammeth et al. developed a sound-limiting infinite compression device that was used for management of debilitating hyperacusis. The loudness suppression devices were housed in in-ear casings and supplied low-level amplification followed by an extreme form of amplitude compression for moderate or high level inputs to reduce loudness discomfort without reducing audibility. (Sammeth et al. 2000).

A typical hyperacusis patient may try using earplugs or ear muffs to limit exposure to sound levels that they consider loud. While the intent is to reduce the level of loud sounds, the effect of using such devices is full dynamic range attenuation which potentially exacerbates hyperacusis thus reducing LDLs over time. FIG. 5 illustrates the relative level change when using earplugs versus using a noise generator. Current best practices treatment focuses on noise generators and counseling; however, patients may have difficulty with the transition from earplugs/earmuffs to a noise generator device and fear any device or method related to amplification.

Currently fittings ignore patient-specific dynamic range. The LDL of non-hyperacusic patients can vary more than 30 dB. Current therapies prescribe the same gain for loud sounds for two patients with the same threshold even if their LDLs differ by 40 to 50 dB. Most fittings either over fit by assuming an LDL that is too high or under fit by assuming an LDL that is too low thus leading to discomfort, frustration, limited use and/or rejection.

The current treatment for hyperacusis includes the use of noise generators and counseling to expand the dynamic range, however an intermediate step with sound protection is needed. This step is counterproductive because wearing sound protection can exacerbate hyperacusis and prevents effective delivery of sound therapy. The invention described below overcomes a major dilemma—the patient's desire to wear sound protection rather than wearing and using a sound-therapy device. Given the shortcomings of current therapies for hyperacusis, what is needed is a therapy that is able to recalibrate the abnormal gain associated with hyperacusis by using the natural plasticity of the auditory system that is specifically tailored to the needs of the specific patient.

SUMMARY OF INVENTION

Patients who suffer a debilitating intolerance to the loudness of everyday sounds, a condition known as hyperacusis, present a unique treatment challenge. Such patients often present in the clinic wearing earplugs (EPs) to limit offending sound exposures. Chronic use of EPs increases auditory gain and exacerbates the hyperacusic condition, rendering the EP wearer even more sensitive to loud sounds. In contrast, chronic use of ear-level sound generators (SGs), which produce low-level noise, act to reduce auditory gain thus increasing tolerance for loud sounds. Treatment that enhances sound tolerance and expands dynamic range allows more linear processing; alleviates the negative aspects of wide dynamic range compression; supports greater sound fidelity; and improves the benefits and usage patterns.

The inventors have developed a method for treating hyperacusis involving a novel transitional device incorporating EPs and sound generators (SGs) and a formal treatment protocol to transition the patient from EPs towards normal audition. To meet the patient's pre-treatment needs, a deeply seated and acoustically sealed in-the-ear mold offers maximum sound attenuation. This mold includes a heat-activated stint that expands at body temperature to augment the normal seal, functioning as a high-quality, custom EP. A miniature behind-the-ear hearing device is connected to the earmold via slim probe tube. The device has four key functions in addition to the attenuation provided by the EP. An on-board SG creates a low-level, spectrally-shaped noise and is configurable for individual patients. The SG also serves to reduce auditory gain and increase sound tolerance. As the SG induces loudness tolerance change, amplification approaches unity gain over time to overcome the maladaptive plasticity associated with earplugs. Simultaneously, output limiting (loudness suppression) reduces the exposure to loud, offending sounds. If the patient has aidable hearing loss, then the device can function as a fully-featured hearing aid.

A fitting protocol has been developed so that the patient can realize the desired benefit of this novel treatment device. During the first fit, real-ear measures quantify unaided gain, occluded gain, the noise response, and the aided unity gain needed to overcome earplugging. Output limiting (loudness compression), imposed under conditions of unity gain, minimizes exposure to loud sounds while providing access to soft and comfortably loud sounds typically attenuated by an EP that otherwise exacerbates hyperacusis. A real-ear noise response is measured and adjusted to the desired spectral shape. The patient undergoes counselling on use, care, goals, and expectations that the low-level noise will enhance sound tolerance. On subsequent visits, the resulting SG-induced increases in loudness tolerance determine the release of loudness suppression and the transition of the patient from EPs to normal device-free audition, ultimately offering an effective treatment for debilitating hyperacusis.

In an embodiment, a method of diminishing hypersensitivity to sound in a patient in need thereof is presented comprising: providing an in-ear hearing device; counseling the patient on loudness suppression and the sound generator; adjusting loudness compression thresholds based on a patient's frequency-specific loudness discomfort levels; fitting the sound generator to the patient by configuring the sound generator to a set level corresponding to a patient-specific soft loudness judgement; and systematically increasing the loudness compression thresholds to transition the patient to normal hearing.

The in-ear hearing device is comprised of two interchangeable earmolds wherein one earmold is closed and another earmold is open wherein the earmolds conform substantially to the diameter and geometry of the patient's ear; a behind the ear shell connected to one of the earmolds by tubing; a receiver, sound generator component, at least one microphone and a signal processing component containing an amplifier all contained within the shell; and fitting software capable of controlling adjustment of noise generation and loudness suppression compression in the hearing device;

The patient may wear either device for as long as can be tolerated by the patient in the waking day, preferably for at least 8 hours per waking day. The open earmold may swapped for the closed mold and may be worn by the patient when in a controlled sound environment where no unexpected sounds are present. The closed mold is worn by the patient when the patient expects to be exposed to an uncontrolled sound environment.

In an embodiment, a method of treating hyperacusis in a patient in need thereof comprising: providing an in ear hearing device; connecting the device to a programming computer; measuring the real ear unaided response (REUR); counseling the patient on the hearing devices; fitting the hearing devices with the closed molds to each ear of the patient; counseling the patient on the sound generator; fitting the sound generator to the patient by configuring the sound generator to a set level corresponding to a patient-specific soft loudness judgement; and systematically increasing the loudness compression thresholds to transition the patient to normal hearing.

The in-ear hearing device may be comprised of two interchangeable earmolds wherein one earmold is a closed mold and the other earmold is an open mold which conform substantially to the diameter and geometry of the patient's ear; tubing connecting one of the two interchangeable earmolds to a behind the ear shell; at least one microphone, a receiver, a sound generator and a signal processor core containing an amplifier electrically connected and contained within the behind the ear shell; fitting software capable of controlling adjustment of noise generation and loudness suppression compression in the hearing device.

Fitting the hearing devices with the closed molds to each ear of the patient may comprise the steps of: positioning each hearing device so that the earmold of the hearing device is inserted into one of the patient's ears wherein one ear is a test ear and the other ear is a non-test ear; estimating a verification noise floor; measuring real ear occluded response (REOR) by muting the sound generator, amplifier and microphones and administering a broadband or white noise from verification system speakers in the test ear; measuring real ear aided response (REAR); adjusting a gain-frequency response so that the REAR matches the REUR curve to achieve unity gain and result in real-ear insertion gain (REIG) that is 0 dB across frequency; adjusting loudness compression thresholds based on a patient's frequency-specific loudness discomfort levels; and repeating the above steps for the other device in the non-test ear.

Fitting the sound generator to the patient may comprise the steps of inserting the one hearing device into each of the test and non-test ears of the patient; activating the sound generator of the hearing device in the test ear of the patient to emit a low-level broadband noise; establishing a level with the patient where the noise is perceived to be comfortable but soft according to the Contour Loudness Test Category 3; varying loudness of the noise and obtaining categorical loudness judgments on the noise from the patient; measuring real-ear sound generator (RESG) level to quantify SG output; repeating above steps for the hearing device in the non-test ear; and balancing both devices.

The method may also include administering audiometric testing to the patient prior to providing the hearing device to the patient. The method may include muting the receiver and amplifier and the at least one microphone of both hearing devices with the sound generator off prior to inserting the hearing devices into the patient's ears.

The sound generator may be calibrated after estimating the noise floor by unmuting the sound generator and administering a white noise stimulus in the test ear.

The data from REOR, REUR and noise floor may be compared to reference data in the fitting software.

The REAR may be measured by the steps comprising: muting the sound generator; unmuting the receiver and amplifier and microphones; administering a broadband or white noise stimulus to the test ear; having the patient categorize loudness of the stimulus; and increasing a frequency of the stimulus at intervals until the patient reports loudness category 6 categorical judgment.

The patient may wear both devices for at least 8 hours per waking day. The open earmold may swapped for the closed mold and may be worn by the patient when in a controlled sound environment where no unexpected sounds are present. The closed mold is worn by the patient when the patient expects to be exposed to an uncontrolled sound environment.

All measurement stimuli are emitted at frequencies about the noise floor. The loudness suppression is released about every 4 weeks.

Both devices are balanced by activating the both devices simultaneously and adjusting each device to have equal loudness.

A system for use in treatment of hyperacusis in a patent in need thereof comprising: a hearing device; fitting software capable of controlling adjustment of noise generation and loudness suppression in the hearing device; verification software capable of connecting with the fitting software wherein the verification software provides reference data for comparison with patient data; and a counseling protocol wherein the counseling protocol provides counseling for both the sound generator and the loudness suppression.

The hearing devices may be comprised of: two interchangeable earmolds wherein one earmold is a closed mold and the other earmold is an open mold which conform substantially to the diameter and geometry of the patient's ear; tubing connecting one of the two interchangeable earmolds to a behind the ear shell; and at least one microphone, a receiver, a sound generator and a signal processor core containing an amplifier electrically connected and contained within the behind the ear shell.

The hearing devices are inserted into the patient's ears and loudness compression thresholds are adjusted based on a patient's frequency-specific loudness discomfort levels. The sound generator is fitted to the patient by configuring the sound generator to a set level corresponding to a patient-specific soft loudness judgement. The loudness compression thresholds are systematically increased to transition the patient to normal hearing.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
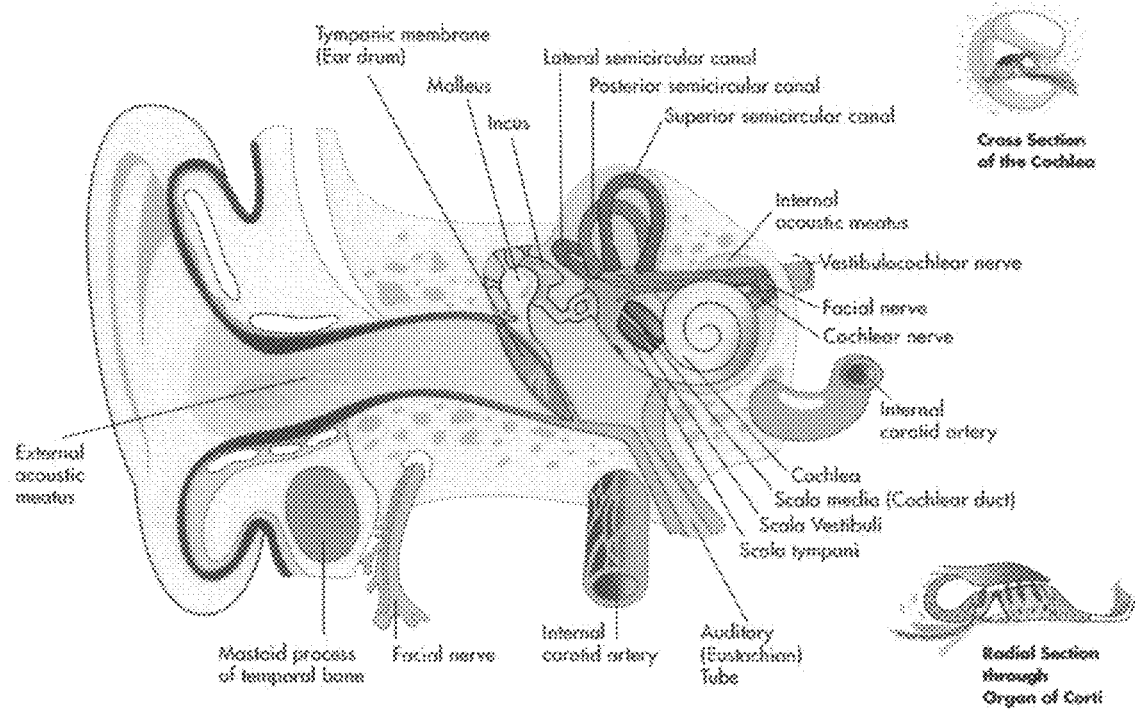
FIG. 1 is an image depicting the anatomy of the human ear.
Figure 2:
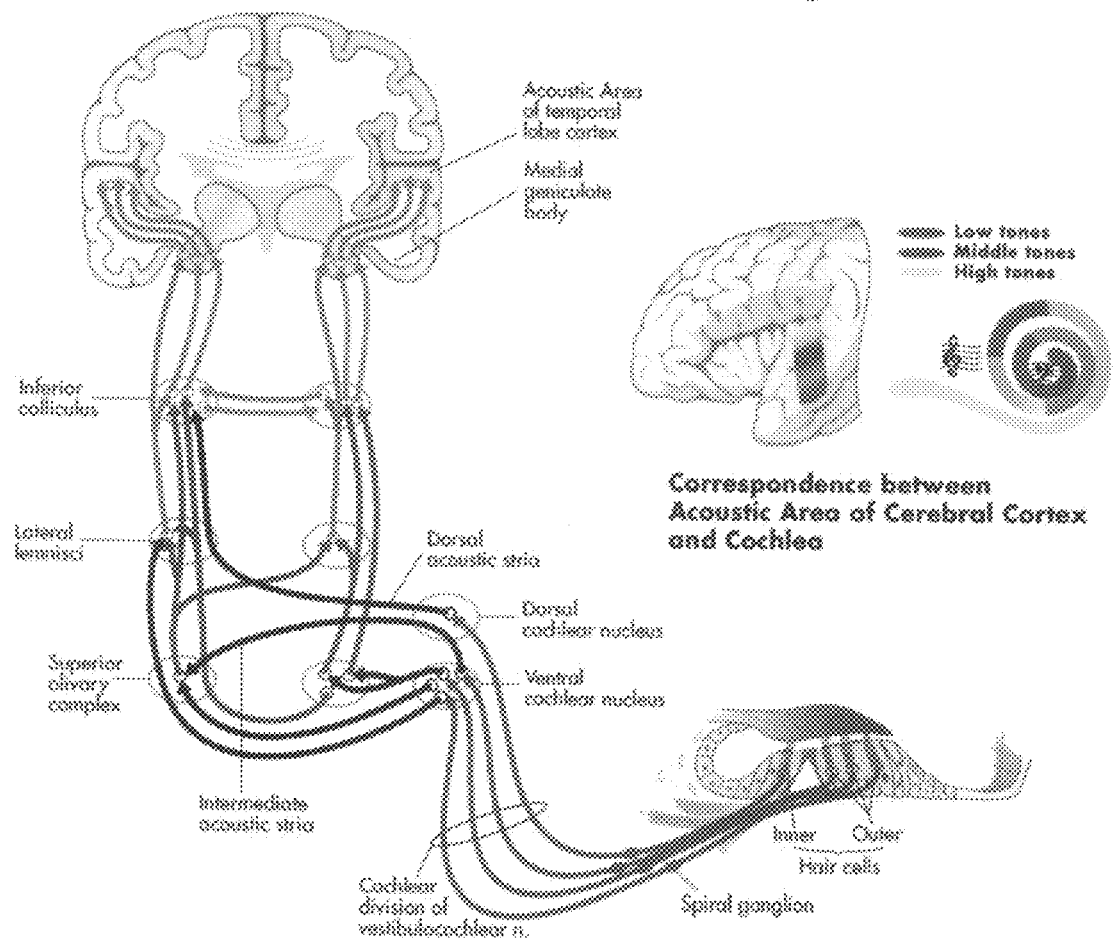
FIG. 2 is an image depicting the afferent auditory pathways.

In the following detailed description of the preferred embodiments, reference is made to the accompanying drawings, which form a part hereof, and within which are shown by way of illustration specific embodiments by which the invention may be practiced. It is to be understood that other embodiments may be utilized, and structural changes may be made without departing from the scope of the invention.

Abbreviations
BTE—behind the ear
CR—compression ratio
CST—connected speech test
D/A—digital to analog
DR—dynamic range
DSP—digital signal processing
EP—ear plugs
HE—habituation of emotional association
HF—high frequency
HR—habituation of physiological response
IHC—inner hair cells
ILD—interaural level difference
IRN—input referred noise
LDL—loudness discomfort levels
LF—low frequency
LS—loudness suppression
NG—noise generator
OHC—outer hair cells
REAR—real ear aided response
REIG—real ear insertion gain
REOR—real ear occluded response
REUR—real ear unaided response
RES—real-ear system
SG—sound generator
SNHL—sensorineural hearing loss SNR—signal to noise ratio
UG—unity gain
WDRC—wide dynamic range compression Definitions Unless otherwise defined, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are described herein. All publications mentioned herein are incorporated herein by reference in their entirety to disclose and describe the methods and/or materials in connection with which the publications are cited. It is understood that the present disclosure supercedes any disclosure of an incorporated publication to the extent there is a contradiction.

The term "about" or "approximately" as used herein refers to being within an acceptable error range for the particular value as determined by one of ordinary skill in the art, which will depend in part on how the value is measured or determined, i.e. the limitations of the measurement system. As used herein, the term "about refers to ±10% of the numerical.

As used herein, the term "comprising" is intended to mean that the products, compositions and methods include the referenced components or steps, but not excluding others. "Consisting essentially of" when used to define products, compositions and methods, shall mean excluding other components or steps of any essential significance. "Consisting of" shall mean excluding more than trace elements of other components or steps.

As used in the specification and claims, the singular form "a", "an" and "the" include plural references unless the context clearly dictates otherwise.

"Patient" is used to describe a human to whom treatment is administered. The terms "patient" and "subject" are used interchangeably herein.

"Sound generator" or "noise generator" are used interchangeably herein to refer to a circuit that produces noise/sounds at various frequencies. In some embodiments, the noise generator is used to provide a constant low-level white noise to the patient through use of the loudness suppression device described herein.

"Earmold" as used herein refers to a device made of pliable material that can be inserted into the outer portion of a human ear and mold itself to the shape of the ear canal.

"Open mold" as used herein refers to an earmold made of soft, pliable material that can be inserted into the outer portion of the ear and having open portions along the base of the earmold to allow some sound to pass through. The flow of sound through the natural or direct sound path is referred to as venting. An open mold has maximum venting.

"Closed mold" as used herein refers to an earmold made of soft, pliable material that can be inserted into the outer portion of the ear. In some embodiments, the earmold contains a body heat activated stint that expands in the ear for a snug fit and occludes the ear canal. A closed mold has minimal venting.

The three most obvious consequences of sensorineural hearing loss (SNHL) are reduced audibility, reduced dynamic range and poor speech understanding. Amplification is normally used to treat reduced audibility and wide dynamic range compression (WDRC) is used to treat reduced dynamic range (DR) and poor speech understanding. However, WDRC increases distortion, decreases signal to noise ratio (SNR) and may distort interaural level differences (ILDs).

Figure 3:
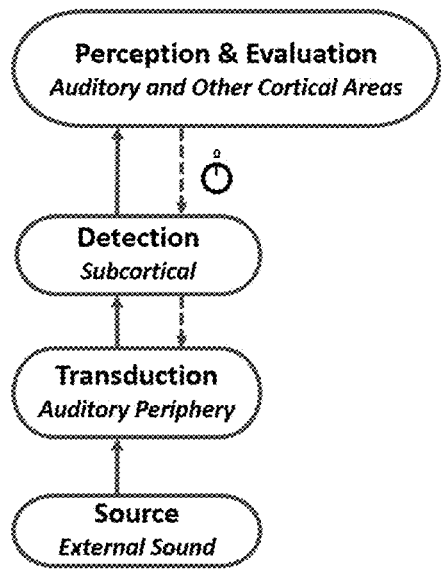
FIG. 3 is a flow chart of the normal-gain system.
Figure 4:
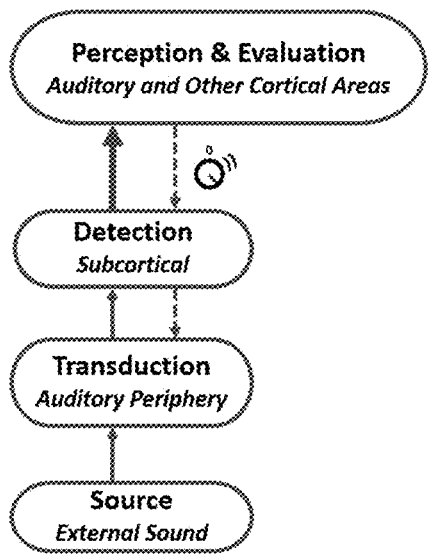
FIG. 4 is a flow chart of the loudness hyperacusis modeled hyper-gain system.
Figure 5:
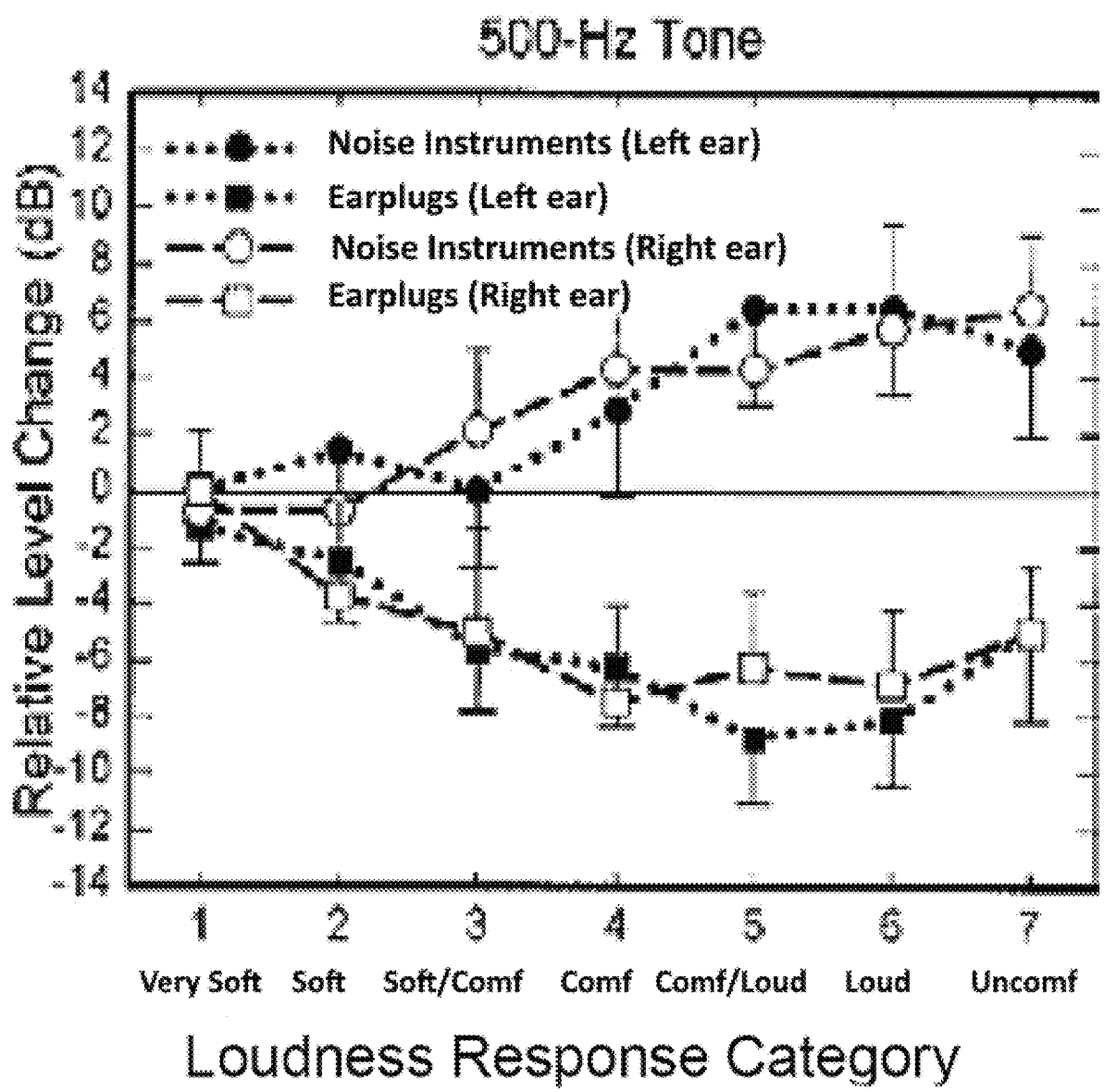
FIG. 5 a graph depicting changes in gain with earplugs versus noise generators. (Formby et al. 2003).

As discussed previously, when there is decreased input to the system or there is some sort of offending acoustic event, damage, or auditory disorder that alters gain, the brain increases the gain to compensate. However, when there's typical input to the system and the ears are working normally, then the brain normalizes the gain. (FIG. 3). The appropriate treatment can be used to retrain or recalibrate the brain to normalize the auditory gain in hyperacusis patients thus restoring normal sound tolerance. (FIG. 4). This retraining process or habituation may be a long process which requires patience over the course of treatment.

Figure 6:
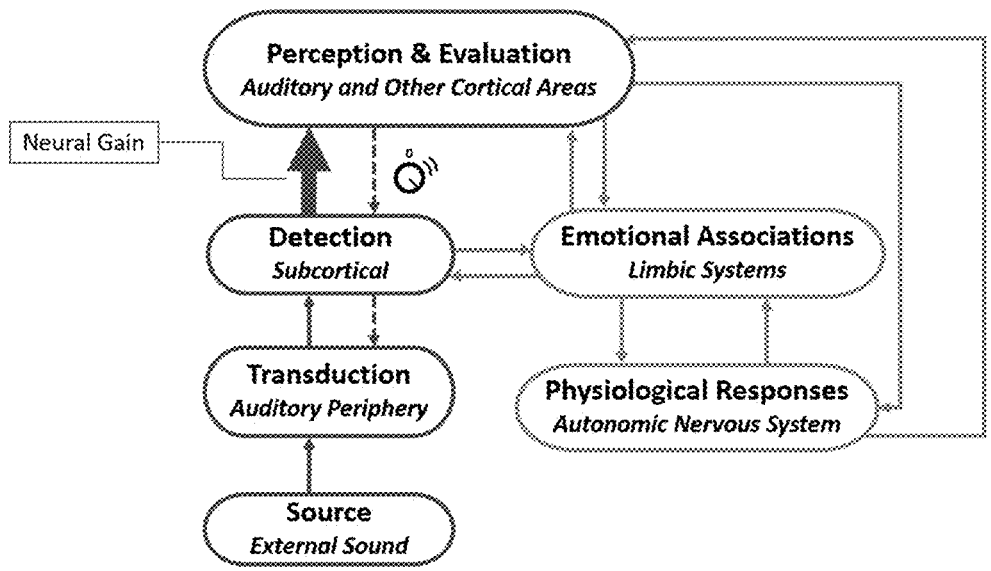
FIG. 6 is a flow chart of the hyper-gain system with emotional associations and physiological responses.
Figure 7:
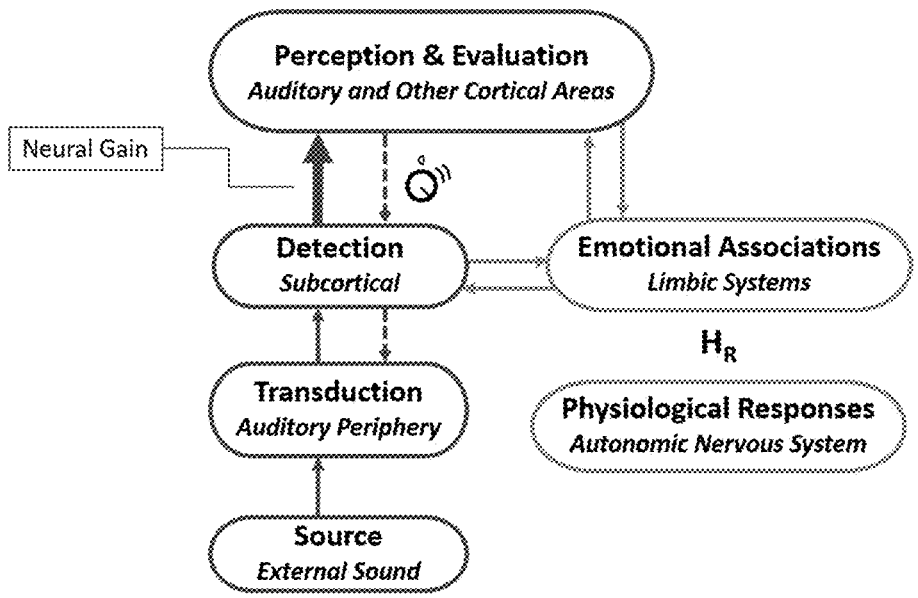
FIG. 7 is a flow chart of the hyper-gain system with emotional associations and habituation of physiological responses.
Figure 8:
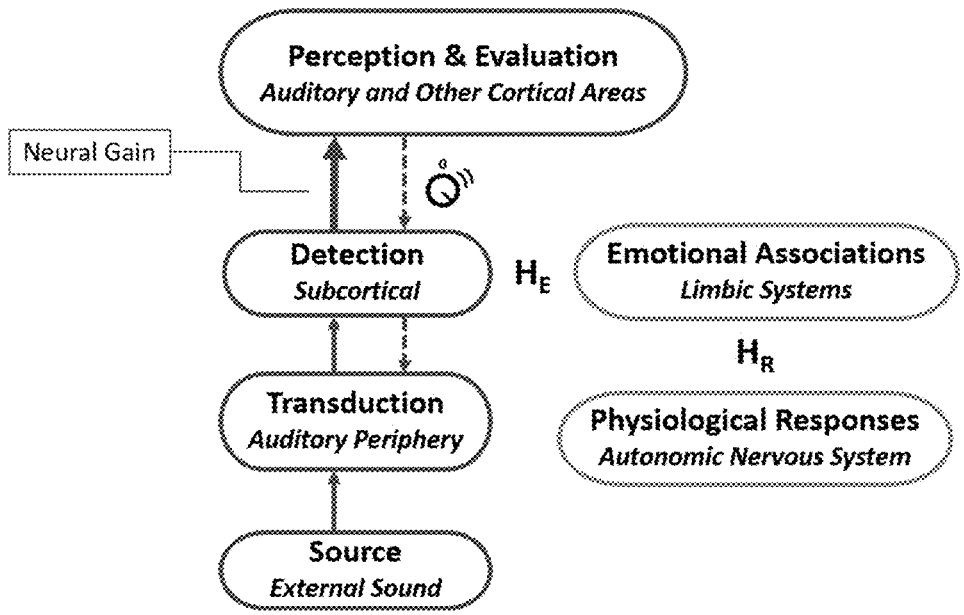
FIG. 8 is a flow chart of the hyper-gain system and habituation of emotional associations and physiological responses.
Figure 9:
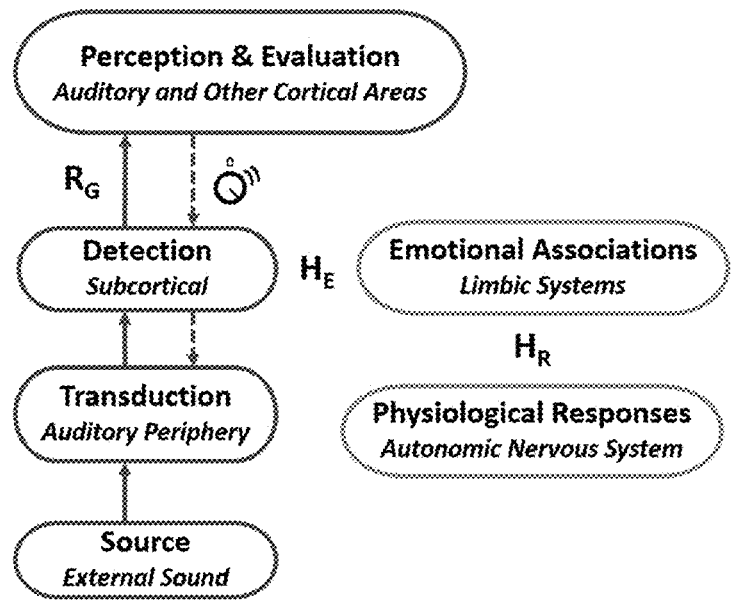
FIG. 9 is a flow chart of the normal-gain system following recalibration of gain and habituation of emotional associations and physiological responses.

The sound therapy treatment described herein breaks or habituates the learned negative connections associated with the provoking sound exposures. FIG. 6 illustrates the hyper-gain system in which both emotional associations and physiological responses are a part of the hyper-gain system. The sound therapy is a passive process, first breaking the connection with the physiological reactions that are controlled by the autonomic nervous system followed by habituation of the patient's elevated emotional associations to sounds, which over time results from habituation of the negative connections with the limbic system. (FIGS. 7 and 8). As these connections are habituated, the gain in the central auditory system is being recalibrated and gradually decreases. As a result, the gain returns toward its normal state, and sounds of all kinds are processed and perceived in a normal way in the high cortical areas. (FIG. 9). The treatment protocol is used to get the patient to a point where sounds are no longer uncomfortable. It is important to mention that the recalibration of the gain is not the direct result of habituation of physiological response (HR) and habituation of emotional associations (HE), but it facilitates the habituation process. The low-level sound therapy and chronic exposure to healthy sound are the principle drivers of the gain recalibration.

Figure 10:
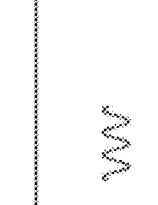
FIG. 10 is a table illustrating how loudness is perceived for individuals with normal sensitivity versus individuals with hyperacusis. The table also illustrates how loudness is perceived when earplugs are worn versus when sound generators are worn.
Figure 11:
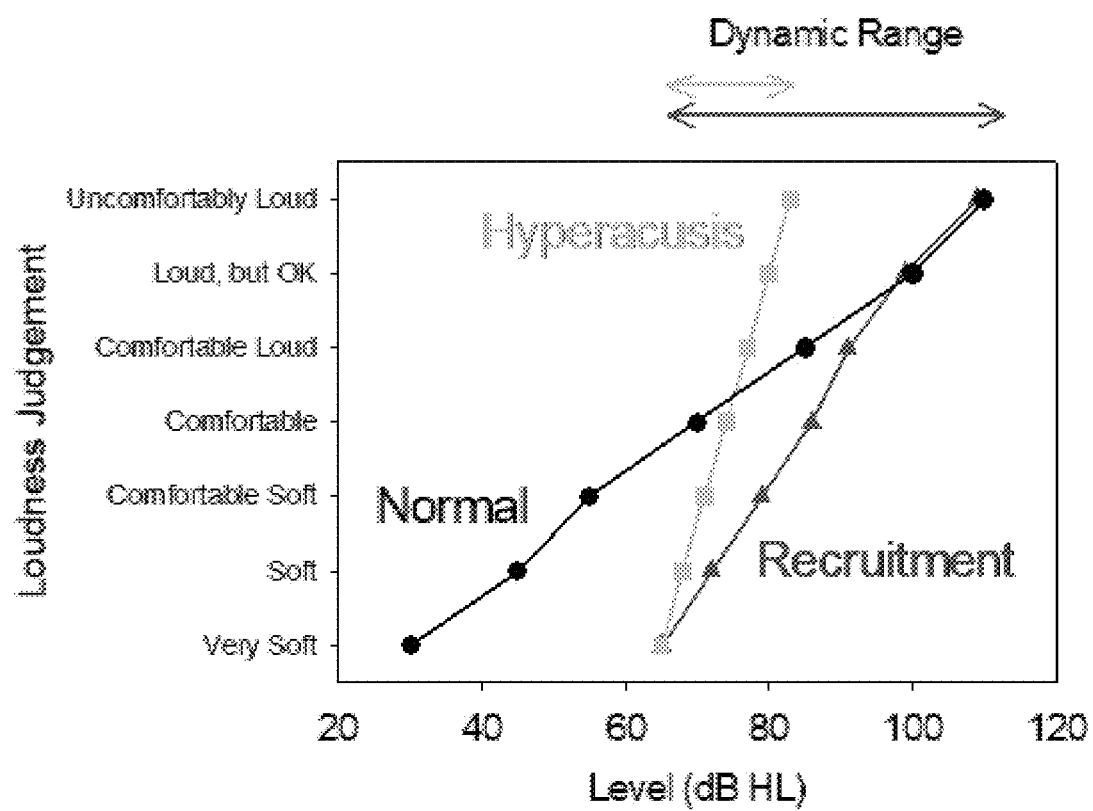
FIG. 11 is a graph depicting recruitment versus hyperacusis. Recruitment refers to "normal loudness" for high sound levels while hyperacusis refers to "uncomfortably loud" for moderate sound levels with an abnormally reduced dynamic range (DR). The image depicts an example of a person with hyperacusis and hearing loss. As noted in the image, the reports do not join the normal curve, but instead reach uncomfortable levels at a much lower level thus the reduced dynamic range is both due to the hearing loss and the lower LDL.

Sound therapy is achieved by exposing the auditory system to a non-annoying, low-level sound. These soft levels are activated by healthy sound exposures, initially under controlled conditions in the patient's home, and with an ear-worn device used in both ears. The device incorporates a sound generator that emits a soft sound similar to what is heard when putting a seashell to one's ear. The device also includes a limiter or compressor that restricts exposure to loud sounds, protecting the patient from offending sounds during treatment. FIG. 10 illustrates how loudness is perceived for individuals with normal sensitivity versus individuals with hyperacusis and how loudness is perceived when one wears earplugs versus using sound generators. Recruitment refers to "normal loudness" for high sound levels while hyperacusis refers to "uncomfortably loud" for moderate sound levels with an abnormally reduced dynamic range (DR). FIG. 11 depicts an example of a person with hyperacusis and hearing loss. As noted in the image, the reports do not join the normal curve, but instead reach uncomfortable levels at a much lower level thus the reduced dynamic range is both due to the hearing loss and the lower LDL.

The patient is given an audiometric test in which the patient is presented with different frequencies of sounds and asked to detect the lowest sound at each frequency which becomes the patient's threshold. When the patient hears a sound during the test, they raise a hand or push a button. An audiogram is formed from the results of the audiometric test which depicts frequencies of sound that are heard by the patient in a graph form. The audiogram depicts how loud sounds need to be at different frequencies in order for the patient to hear them. The audiogram illustrates the type, degree and configuration of hearing loss. A marker, such as a dashed line, at 20 dB shows the limit of normal hearing. If the patient's thresholds are below this dashed line then there is some degree of hearing loss. The farther the patient's thresholds fall below the dashed line, the greater the hearing loss. On average, young normal hearing people have their thresholds at 0 dB. In the audiogram, one color, for example a red color, is used to depict results for the patient's right ear and another color, for example a blue color, is used to depict results for the patient's left ear. Alternatively, two different audiograms can be used, one for the right ear and one for the left as in FIG. 12. On the x-axis, the frequencies, which correspond to the perceived pitches of the sounds are measured in Hertz. The low frequencies located toward the left represent sounds such as the vowels "aa, oo" while the high frequencies located toward the right represent sounds in speech such as the consonants "ss, sh". The y-axis is used to measure the intensity of the sound in decibels, i.e. the amount the level of the sound had to be increased for the patient to hear it. Going downward on the vertical axis the intensity increases as shown by the increasing decibel values.

Speech tests are also performed on the patient to demonstrate the ability to detect speech and understand it at conversational levels. The speech reception thresholds closely agree with hearing thresholds at the primary frequencies that are critical in understanding speech. Results of the speech tests are given in the context of the percentage the patient was able to understand and repeat the number of words presented at a conversational level. This information is important especially for hearing aid fitting.

Figures 13, 14:
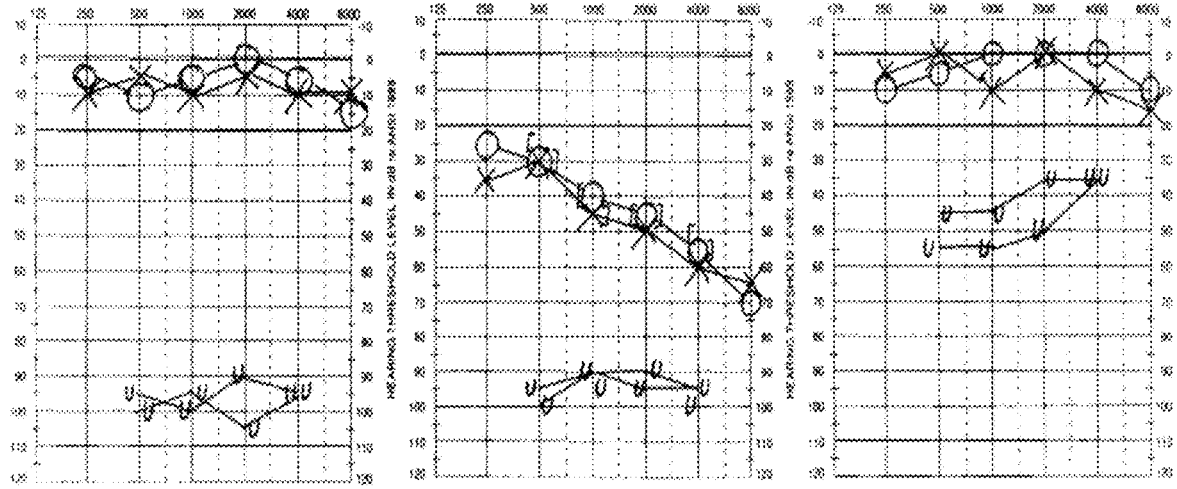
FIG. 13 is a series of exemplary audiograms depicting audiometric thresholds and LDLs, bilaterally, for individuals with normal hearing sensitivity and typical sound tolerance, sensorineural hearing loss with loudness recruitment, and hyperacusis with normal hearing sensitivity. Pure tone thresholds are shown for the left ear by the cross or X symbols and for the right ear by the circles. Uncomfortable listening levels (UCL) are indicated by the U symbols. The figure on the left represents normal hearing with a normal dynamic range. The figure in the middle represents mild sloping to moderately severe sensorineural hearing loss with a reduced dynamic range due to hearing loss. The figure on the right represents normal thresholds and reduced dynamic range due to hyperacusis (Sandlin and Olsson, 1999).
FIG. 14 is a table illustrating dynamic range versus loudness hyperacusis. Sensitivity to sound/hyperacusis is defined as a dynamic range less than 60 dB. (Goldstein et al. 1996).

In addition to measuring the patient's ability to detect sounds and understand speech, sound tolerance was measured by making the sound louder and louder until the patient reported the sound as uncomfortable. These measures are referred to as loudness discomfort levels (LDLs). LDLs represent the levels at which sounds were intolerable for the patient's threshold at each frequency and are shown by the "U" symbols at each frequency. (FIG. 13) The range between the threshold, where the patient barely heard the sound and the "U" symbol, where the sound became uncomfortable, is the dynamic range. Usually, these LDLs are around 100 dB HL for most individuals. When the LDLs are lower than about 90 dB, individuals may have problems tolerating louder sounds. Hyperacusis can manifest with reduced LDLs at all frequencies and in both ears. For example, a patient may have thresholds that are normal, so they can hear soft sounds at a soft level, but as the intensity of sound increases, a level is reached quicker than usual and becomes uncomfortable, which accounts for the patient's limited dynamic range and explains intolerance to moderate and loud sounds. As the patient regularly exposes his/her system to healthy sound through the sound therapy protocol, the LDLs increase with time and the patient's adverse reaction to sounds slowly subsides as the hyperacusis condition improves.

If the patient has hearing loss with loudness-based hyperacusis then they may have some hearing loss that requires a higher than normal level to hear soft sounds, and then as the intensity of a sound increases, a level is very quickly reached where sounds may become uncomfortable. Because of the hearing loss, the patient would have a limited dynamic range that contributes to intolerance to moderate and loud sounds. If the patient uses a hearing aid then it will amplify sounds (it will make them louder) at different frequencies, which may become loud and uncomfortable thus limiting how much amplification can be used.

Counseling plays an important role in treating hyperacusis, as this debilitating condition may cause extreme life changes and may sometimes lead to suicide for some people. While assessing patients with hyperacusis, using a slow pace is crucial. Together, the counseling and the sound therapy create the synergistic conditions needed to activate the habituation and recalibration processes that restore the normal-gain system and restoration of normal LDLs and sound tolerance.

The inventors have developed a system and method for patients suffering from hyperacusis including hearing loss, reduced sound tolerance and restricted dynamic range resulting from primary hyperacusis, hyperacusis associated with misophonia or photophonia, and hyperacusis with or without hearing loss. Exposure to safe, healthy sounds over time decreases the auditory system's gain and improves the patient's tolerance to sounds. The method uses the plasticity of the auditory system to increase the patient's LDLs and to ensure that the patient is comfortable with all kinds of sounds, as was the case prior to the hyperacusis. The treatment is patient-dependent, meaning that amount of use of the devices may differ for each patient in order to receive the treatment benefit. The system uses a novel in-ear device having both loudness suppression and a sound generator for sound therapy in conjunction with a specific counseling protocol and fitting protocol that is patient-specific. The treatment involves counseling and exposing the patient to a healthy sound environment, including to low level, broadband sound from ear-worn devices that will initiate plastic changes within the patient's auditory system. The goal of the treatment is to increase the patient's LDLs to normal levels thus expanding the dynamic range (range between the patient's thresholds and uncomfortable levels) and allowing the patient to hear soft, moderate and loud sounds normally. The expanded DR can be shown by incremental shifts in LDL values.

Briefly for the adaptive hearing aid fitting (AHAF), an existing earplug is replaced with an earmold that functions as a high quality plug that is connected to a device having loudness suppression as well as a sound generator and amplification (hearing aid). Initially, amplification is used to achieve unity gain with no attenuation implemented unless necessary. The patient's full dynamic range is respected, and output limiting is relied on to reduce exposure to loud sounds (loudness suppression). The sound generator is relied on to expand the dynamic range over time with the loudness suppression systematically released as the dynamic range expands. The patient is gradually weaned off of earplugs, muffs, and loudness suppression. An expanded dynamic range also increases the possibility of amplification with comorbid hearing loss.

System Design

Real-ear verification is important due to the differences in ear canal resonances that are caused by differences in shape, size and elasticity of individual patients; differences in concha/pinnae resonance effects and inadequate control of coupling/venting with prescribed settings. It has been shown that without real-ear verification, 74% of reference fittings vary from the prescription by 10 dB or more at one or more frequencies. Real-ear verification leads to increased patient satisfaction, improved audibility, objective documentation of device performance and a lower rate of return.

Earplugs are counterproductive for treatment as earplugs reduce the sound input to the brain and the brain compensates to the reduced input by increasing the gain. The goal of the therapy is to protect the patient's ears appropriately and to use ear protection only when the patient is exposed or expects to be exposed to loud sounds that may harm hearing. The devices limit the patient's exposure to offending sounds that are uncomfortable, thus earplugs should be unnecessary during treatment.

Device Design

Figure 15:
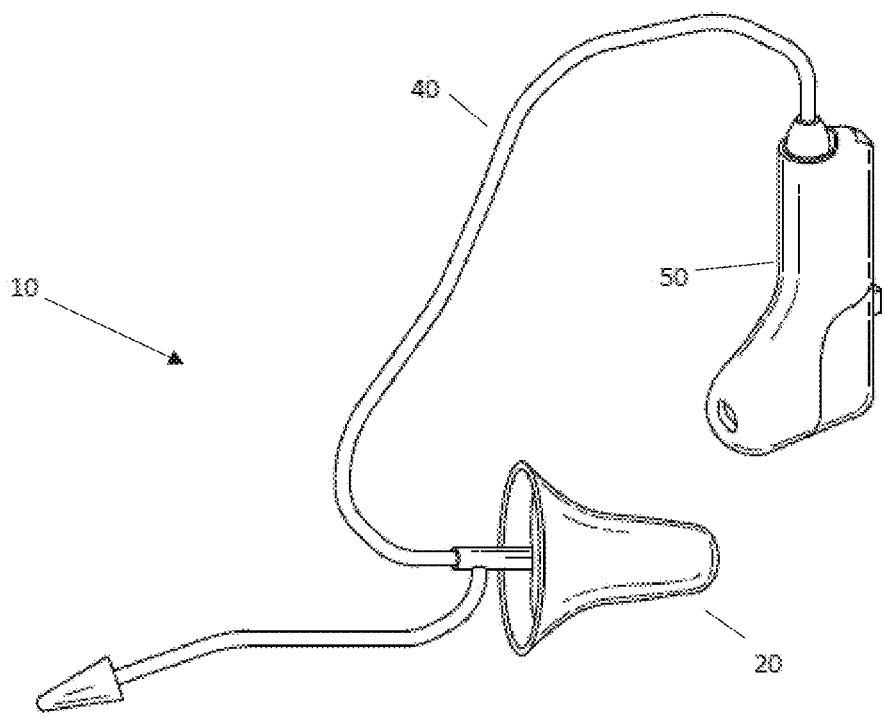
FIG. 15 is a perspective image of the device showing a closed mold earmold.
Figure 16:
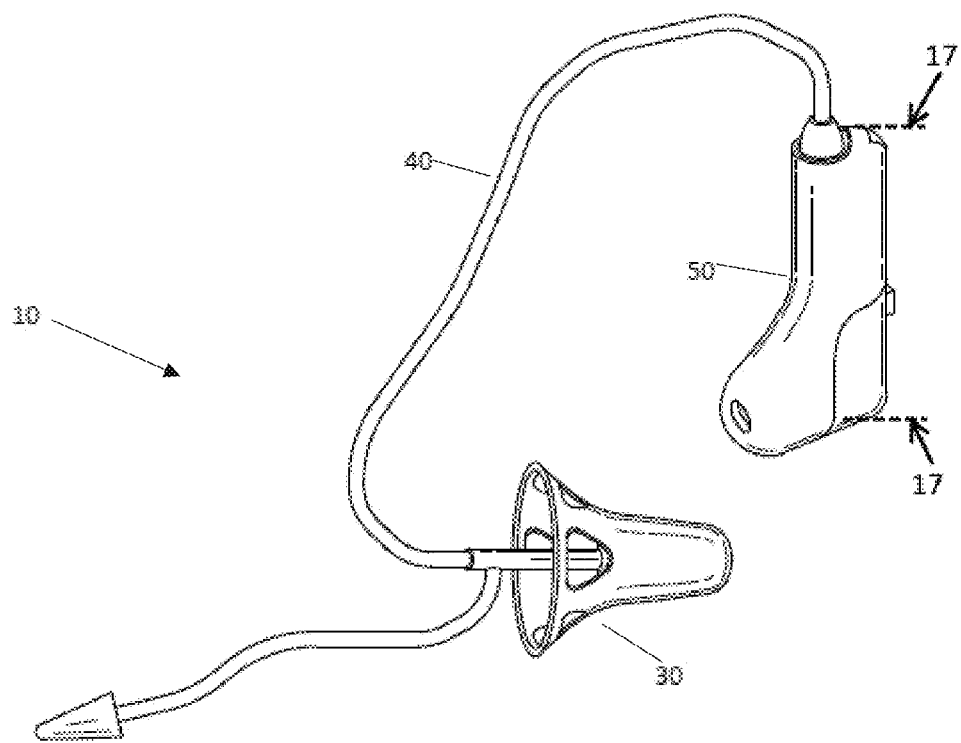
FIG. 16 is a perspective image of the device showing an open mold earmold.
Figure 17:
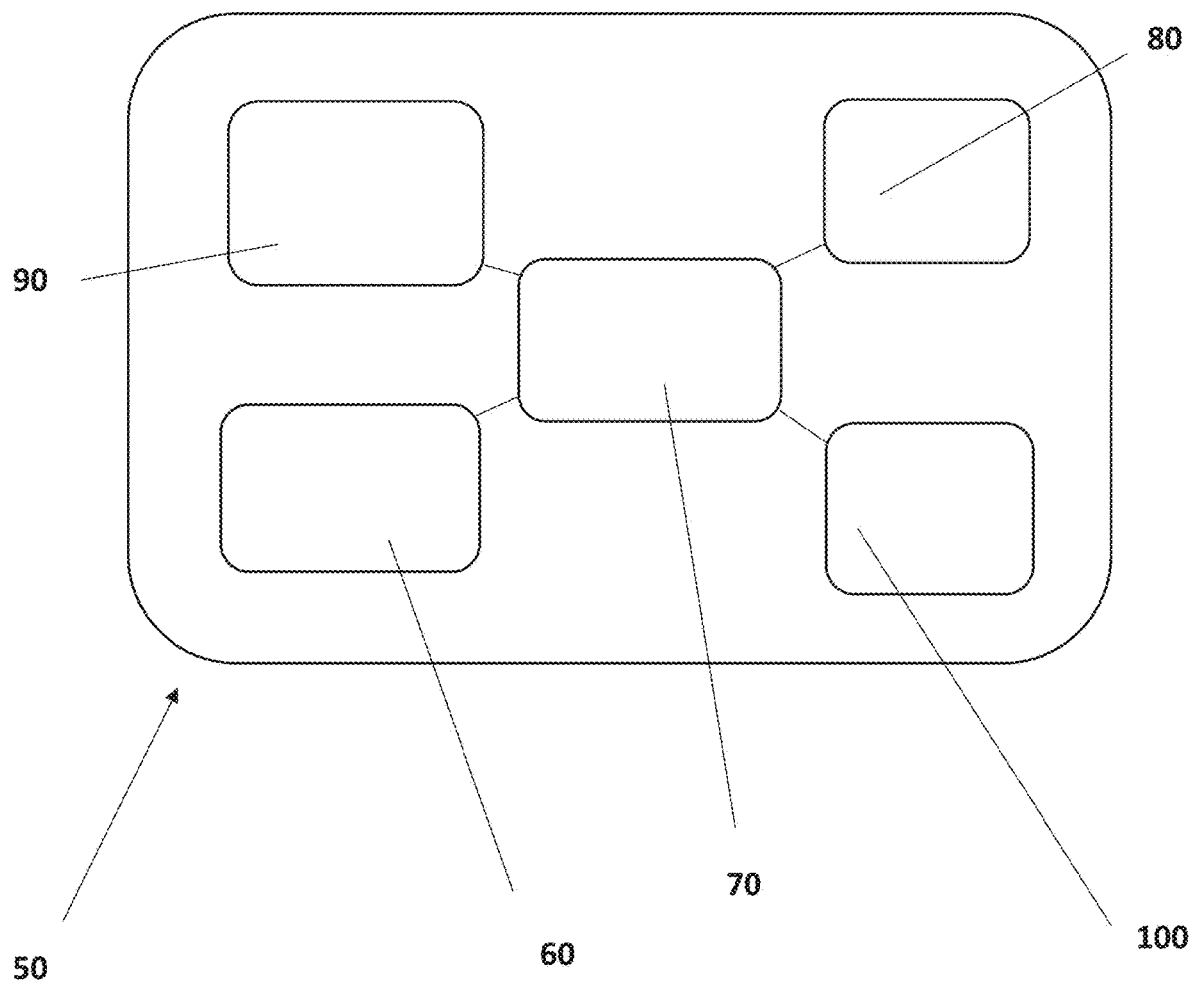
FIG. 17 is a cross-sectional image taken along line 17 of FIG. 16 depicting the components located within the behind the ear shell of the novel device.
Figure 18:
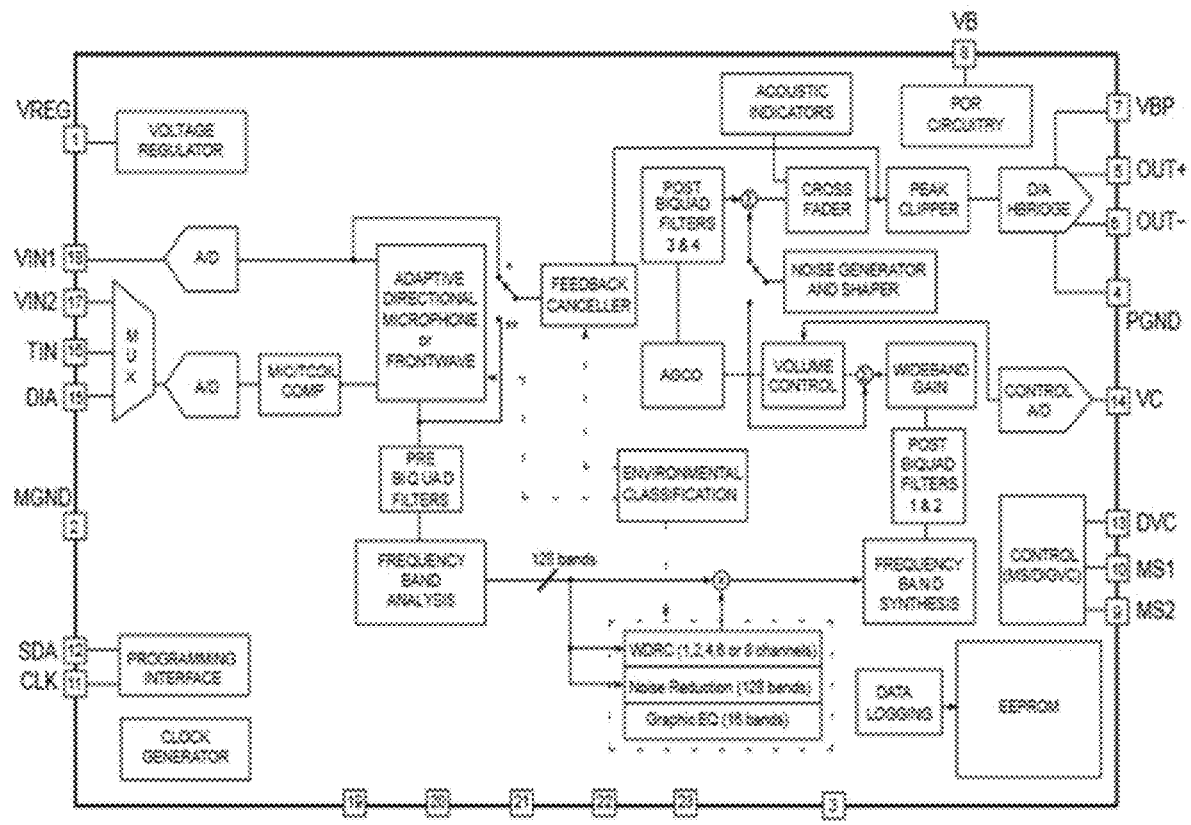
FIG. 18 is an image of an on-semi chipset of the signal processing core in which the noise generator, amplifier and loudness suppression are signal processing features executed on the chip.

The novel device described herein is capable of offering hyperacusis patients a fully integrated instrument capable of spanning continuum of management and treatment from sound attenuation to enrichment. As shown in FIGS. 15 and 16, the inventors have engineered a behind-the-ear (BTE) loudness suppression (LS) device 10 with slim tubing 40, being about 0.9 mm, that supports two interchangeable earmolds. The signal processing core containing an amplifier 70 is combined with a ferrofluid receiver 90 and at least one MEMs microphone 80 housed, along with a battery 100, in a BTE shell 50. (FIG. 17). In some embodiments, at least one MEMs microphones 80, receiver 90 and noise generator 60 are separate components that are electrically connected to the signal processing core chip containing an amplifier 70 via wires as shown in FIG. 18.

Figure 19:
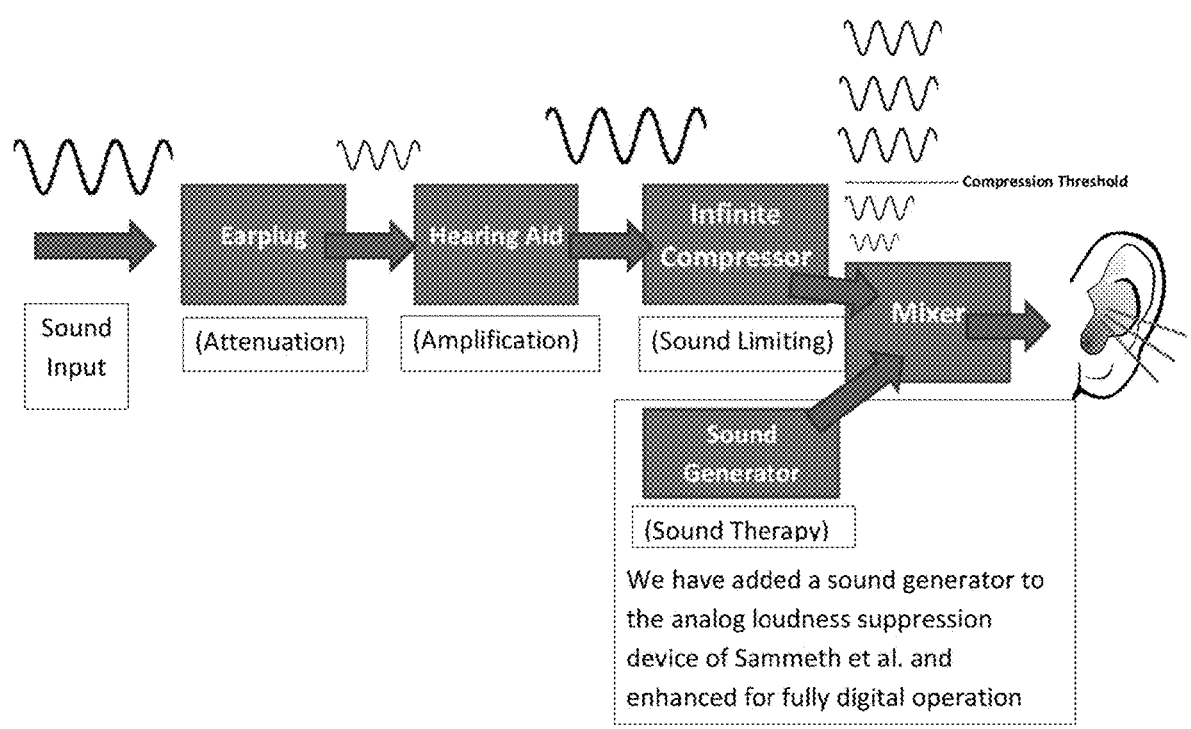
FIG. 19 is an image depicting how sound travels through the device.

The primary "closed" mold 20 comprises an earmold that includes a patented body-heat-activated expanding stint provided by General Hearing Instruments (GHI). (FIG. 15). This technology improves comfort while maintaining a tight seal in the canal to increase passive attenuation. A sound generator (SG) 60 is contained within BTE shell 50 to generate noise. With device 10, subjects can receive the required attenuation with an ear plug function when device 10 is powered off or muted and active loudness suppression (LS) via output limiting compression and sound therapy via sound generator (SG) treatment. FIG. 19 depicts how sound flows through the device.

The secondary open mold 30 minimizes sound attenuation, preserves SG acoustic characteristics, and allows healthy environmental sound exposure (without compression) as desired by the subjects in safe quiet environments that they can control when LS is not needed. (FIG. 16). The ability to use two swappable earmolds promotes the use of the therapeutic sound generator 60 as frequently as possible while providing either attenuation of offending sounds or healthy exposure to comfortable sounds.

Shells include a reusable and pluggable probe-microphone tube port to enable in-situ measurement and calibration of key electro-acoustic parameters.

It is noteworthy that if a loudness suppression device had substantial venting then loud sounds would enter the direct sound path and the LS would be ineffective. With maximum attenuation followed by unity gain, the loudness of sounds below the LS threshold is not altered (unity gain) and the loudness of sounds above the LS threshold can be suppressed via output limiting by an amount equal to or less than the attenuation. With this device, patients are able to receive the required LS compression as well as sound generation treatment together in one device.

Unity Gain (UG) Algorithm

The unity gain is the frequency specific gain sufficient to overcome earmold attenuation. A unity gain-frequency model is used in the device that compensates for the primary occlusion attenuation (i.e., insertion loss) provided with the closed mold. The iterative algorithm measures the real-ear occluded response (REOR) and automatically adjusts gain to achieve the original real-ear unaided response (REUR).

$$REOR(f)=REUR(f)+\alpha(f)$$

$$UG(f)=REOR(f)+\gamma(f)$$

where f=frequency, α=attenuation, and γ=gain.

REUR (natural gain) and REOR (earplug effect) are measured to compute the unity gain with REUR+Precise Gain Adjustments=REAR→Unity gain.

Figure 20:
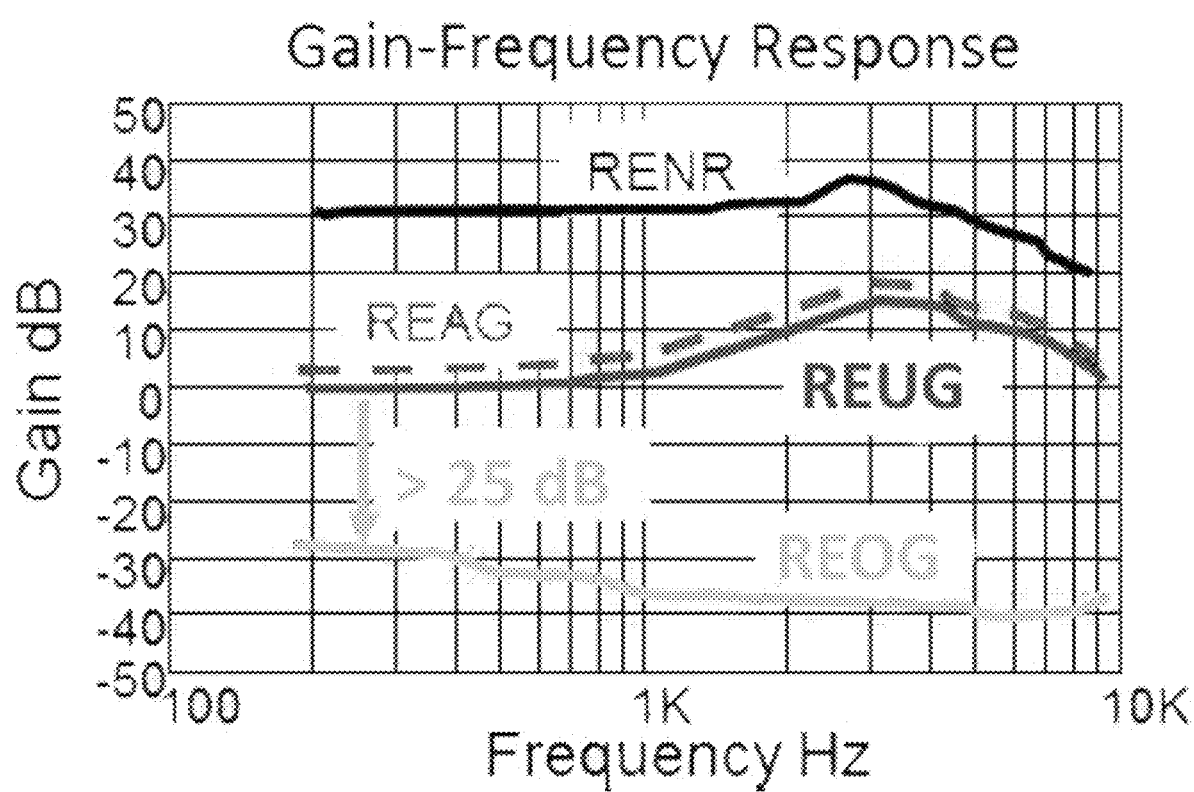
FIG. 20 is a hypothetical graph depicting real ear measures capturing unaided gain (REUG), device occlusion (REOG), aided unity gain (REAG) and noise generator response (RENR).
Figure 21:
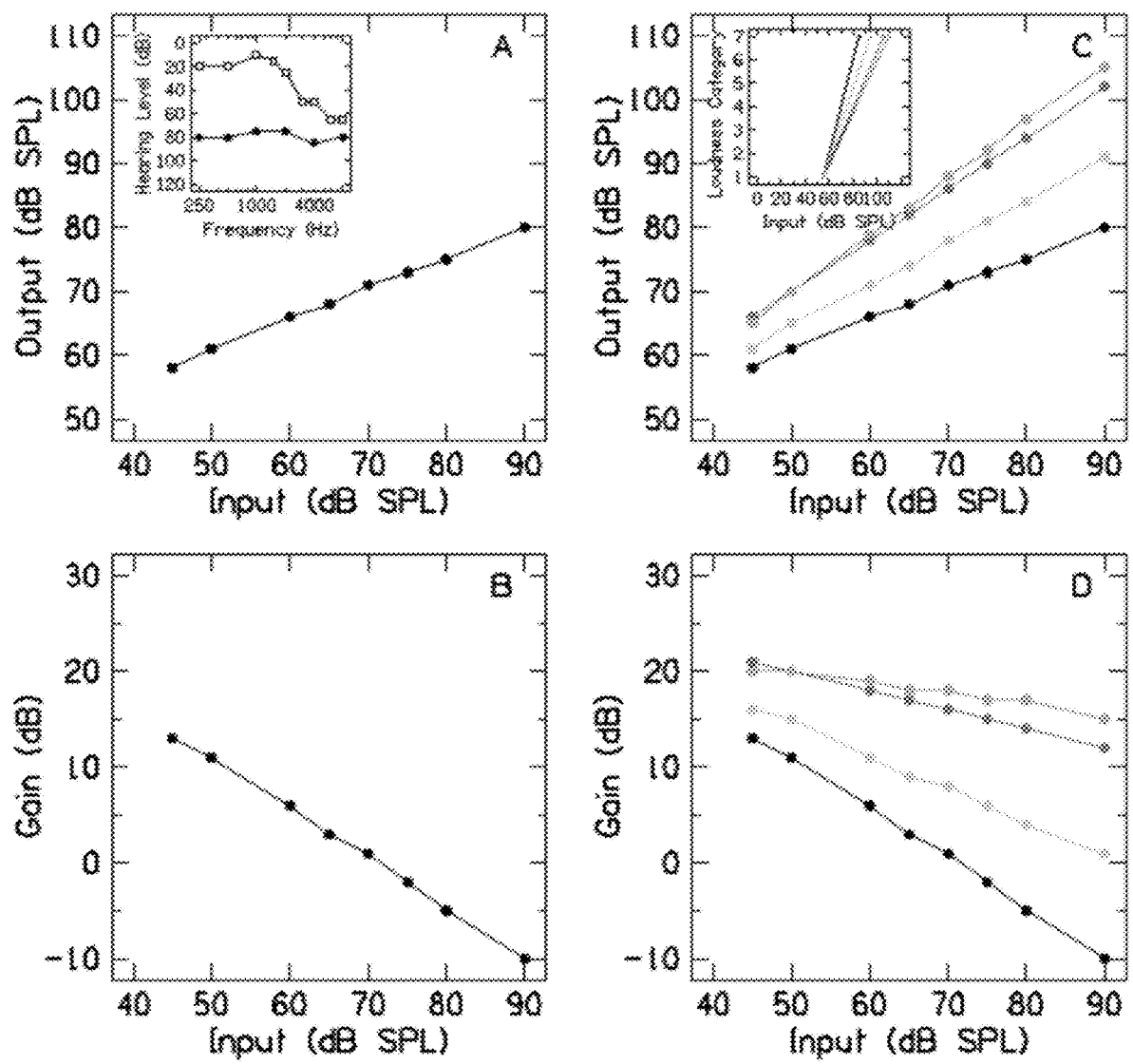
FIG. 21A-D are a series of images depicting an adaptive hearing aid fitting (AHAF) strategy, designed to increase prescriptive gain progressively and incrementally as the hearing-aid user's dynamic range (DR) expands over the course of a proven sound therapy intervention, with the input/output and gain prescription using DSL 5.0 (4000 Hz). (A) input/output rated response; (B) companion input/gain function; (C) corresponding color-coded family of time dependent and treatment driven input/output functions; (D) associated family of gain functions. The AHAF protocol can be modeled using the example of a sensorineural hearing-loss patient, RR, from Formby and Gold (2002). AHAF begins with current best practices (BP) fitting per the Desired Sensation Level (DSL) m[i/o] algorithm, which is the most widely accepted prescriptive strategy incorporating actual LDL judgments. Shown in the left column is the BP fit based on audiometric and LDL data for RR prior to sound therapy. Inputs to the DSL algorithm, taken from the panel A inset, are his measured pure-tone thresholds and LDL values at 4000 Hz. The resulting input/output (i/o) aided response is shown in panel A and the companion input/gain function is shown in panel B after DSL prescriptive fitting of target gain per BP. Following the same BP procedures, shown in the right column are the actual sound-therapy-induced changes in LDL values measured at 4000 Hz for RR, which are now used as the input values to the DSL prescription. These LDL values, measured at four time points during sound therapy, are depicted in the panel C inset as a set of color-coded idealized loudness growth functions; the respective functions highlight the incremental sound therapy-driven changes in the DR. The corresponding color-coded family of time-dependent, treatment-driven i/o functions is shown in the main panel C and the associated family of gain functions prescribed by DSL is shown in panel D. Clearly, over the course of the sound-therapy treatment for RR, the prescriptive output increases systematically more for high-level sound inputs and less for low-level inputs, while aided gain changes from strongly nonlinear (negatively sloping) towards linear (flatter) as a consequence of the treatment-driven changes in the DR.
Figure 22:
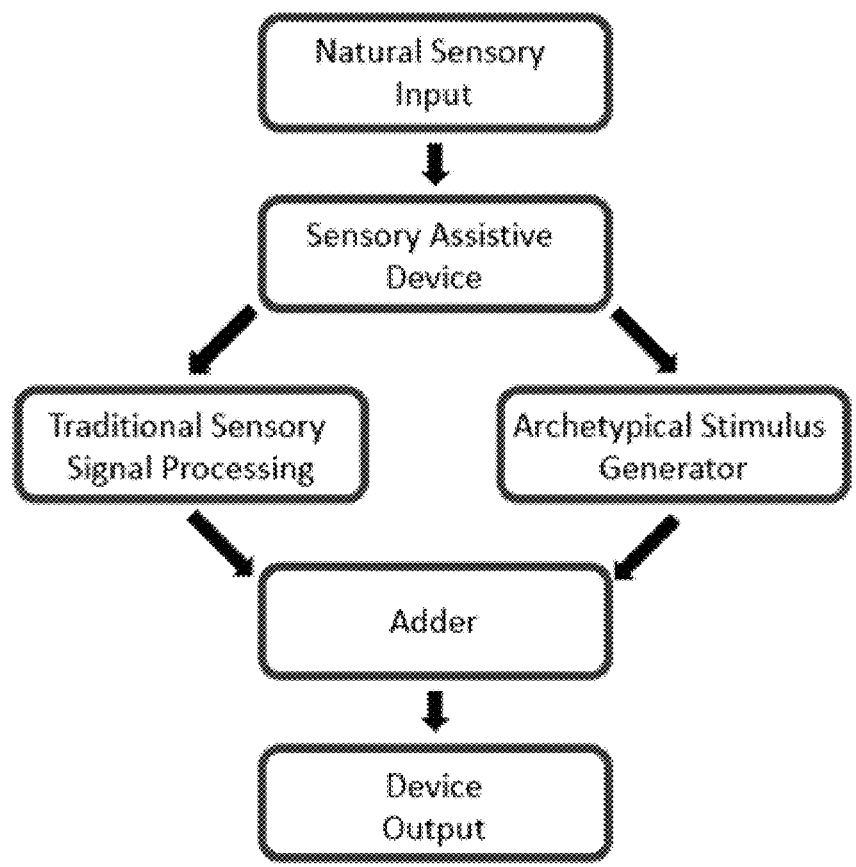
FIG. 22 is a flow chart illustrating a generic implementation of targeted feature-specific sensory therapy.

Device performance is documented for each subject via real-ear measurement techniques shown in FIG. 20. Closed-mold insertion loss is measured as the Real Ear Occluded Gain (REOG; light grey curve). This attenuation will vary by frequency and should be ~25 to 30 dB at low frequencies and up to 40 dB at high frequencies. Real Ear Unaided Gain (REUG; grey curve) provides the basis of the UG target curve for each subject. Individual shaping of the UG condition to offset insertion loss is recorded as the Real Ear Aided Gain (REAG; dashed curve). Closed-loop auto adjustment of filtering controls achieves a match to target +/−2 dB from 200 to 5000 Hz and +/−4 dB from 5000 to 10,000 Hz. The "kneepoint" compression threshold for activating LS is set based on individual, frequency-dependent loudness judgments and verified using test-box measures. In-situ verification of NG output produces the Real Ear Noise Response (RENR; black curve). Overall NG level is calibrated within +/−2 dB of the target frequency response.

Loudness Suppression (LS) Compressor

The digital signal processing (DSP)-based solution uses n channels of amplitude compression in conjunction with more sophisticated attack and release algorithms, thus reducing potential activation/deactivation annoyance. Using a feedforward architecture, (output compression), any algorithmic modification to the signal path is subject to LS compression via output limiting, thereby guaranteeing no risk of over-attack phenomena, even when implementing an infinite-to-1 compression ratio (CR) thereby overall performance is improved when operating as a loudness suppression (LS) device. The LS compression threshold will be adjustable and more than capable of replicating the 65-dB limiting threshold reported by Sammeth et al. In practice, the LS compressor parameters of kneepoint as a function of frequency and ratio as a function of frequency are adaptive over time based on treatment-induced changes in loudness perception. The use of this LS processing in this invention is uniquely tied to the treatment-induced changes in loudness discomfort levels that are measured periodically and used to progressively release the LS by adjusting the frequency-dependent kneepoint according to the magnitude of the treatment effects derived from the unique combination of the counseling and SG use.

Therapeutic Sound Generator (SG) Algorithm

Devices include a broadband SG algorithm, with filtering to fine tune the spectral shape and output levels to match the closed- and opened-mold conditions within subject, user-specific comfort levels corresponding to categorical loudness judgements of "soft but comfortable", and a user-control toggle to allow participants to make small (e.g., ±3 dB) adjustments in noise level as needed and/or to briefly mute the device. The function of the SG is to induce changes in auditory processing that lead to increased sound tolerance and expanded dynamic range over long-term SG use. SG use is the primary therapeutic agent of this invention.

Low-Noise System

Because many individuals with hyperacusis and other sensory tolerance issues may have normal hearing sensitivity as measured by detection thresholds, a low-noise system is desired as system noise would otherwise be audible and potentially bothersome when and if the device is used without the SG active. Main sources of unwanted noise are microphone circuit noise and digital-to-analog (D/A) converter noise. Microphones with input-referred noise (IRN)

levels of 25 to 27 dBA are used. Since D/A noise is proportional to the maximum device output level, a lower-power receiver is used to alleviate this risk. The low-gain nature of these devices should result in noise levels close to imperceptible. If it is determined that the noise level is too high, then a low-level expansion algorithm can be used to attenuate further the device self-noise in quiet environments.

Data Logging

Data logging records usage (hours) separately for the closed- and opened-mold conditions to monitor protocol compliance and ambient sound levels for each condition. Device data logging is an important component in the process of determining treatment dosage.

User Controls

Inclusion of a toggle switch supports adjustment of SG level and inclusion of a "panic" button allows the user in the primary LS mode to disable UG, effectively reverting to maximum attenuation from a well-fitted EP.

Treatment Protocol Description

The treatment protocol consists of five main elements: evaluation, sound generator counseling, loudness suppression counseling, loudness suppression device fitting, and sound generator device fitting. The protocols for each will be described below.

Evaluation Protocol

The first of five key elements of the treatment protocol is the evaluation protocol. The evaluation protocol includes a full audiometric and hyperacusis evaluation. Audiometric evaluation is needed to provide indices of hearing sensitivity needed for device fitting and counseling. Tone decay assessment is performed to ensure that perception of the therapeutic SG will be maintained for prolonged periods of time. The presence of abnormal tone decay is a contra-indication of this treatment. Frequency-specific and ear-dependent loudness discomfort levels (LDLs) are measured and used as input parameters to the LS device algorithm. If LDL measurement is contraindicated, then loudness category six values can be used on the basis of the Contour Categorical Loudness test (Cox et al. 1997).

TABLE 1

CONTOUR CATEGORICAL LOUDNESS SCALE

| Level/Category | Loudness Category Description |
| --- | --- |
| 1 | Very soft |
| 2 | Soft |
| 3 | Comfortable/soft |
| 4 | Comfortable |
| 5 | Comfortable/loud |
| 6 | Loud, OK |
| 7 | Uncomfortable |

The evaluation protocol should also include one or more questionnaires that evaluate, at a minimum, loudness tolerance and quality-of-life to be used on the counseling portion of the treatment protocol.

Counseling on Sound Generating (SG) Devices

The primary purpose of the sound generator (SG) is to expand the patient's loudness tolerance. It is important that the SG counseling precedes LS counseling. The SG component of the devices provides a soothing, seashell-like background sound that provides minimal but constant stimulation to the auditory system including the parts of the brain that are involved in processing and interpreting sound. Prolonged use of SG devices increases loudness tolerance in patients with hyperacusis, even when they have normal hearing thresholds or hearing loss. The SG is set to a soft, comfortable level during the fitting process and works the same way with either of two different ear mold systems (open or closed). The more the patient uses the SG, the greater the improvement in loudness tolerance. Improvement in loudness tolerance is the primary goal of this treatment. Secondary goals include reduced use of attenuating devices and the ability to comfortably experience a wider range of sound levels in normal daily life.

SG Device Use

After acclimating to treatment, the devices should be worn for a minimum of 8 hours each day or longer if comfortable. It is advised to wear the devices as long as possible during the waking day, preferably for a minimum of 8 hours which do not need to be consecutive hours. The open mold is used only when the patient is in a quiet environment where they can control their exposure to uncomfortably loud sounds. The closed mold is used when there is a risk of the patient being exposed to loud sounds. The protective loudness suppression feature works only with the closed mold whereas the sound generator is used with both the open and closed molds to provide treatment. The output of the devices are preset so there is no volume control for the patient to adjust. It is preferable for the patient to avoid unnecessarily removing and inserting the devices multiple times a day. The patient may or may not hear the sound generated by the treatment devices over time, either of which is a normal process.

It is preferable to keep a low level of neutral sound on at all times, day and night, in addition to the sound generators, to avoid silence. Sound therapy from the sound generators can be reinforced by the use of healthy environmental sound from other sources such as fans, sound machines, air conditioners, nature recordings, humidifiers, fountains, aquariums, sound pillows, etc. There always should be healthy sound exposures for the auditory system, which are critical for maintaining normal sound tolerance. The volume of the devices are preset to a soft level that is just above the point where the patient starts to hear it. Once the volume is set, the patient is unable to adjust it until the next clinic visit so it is important that an acceptable volume is set for each of the devices so that the patient experiences equal loudness for both ears. The patient may stop hearing the noise sound from the treatment devices after a short period of time as it is normal for the brain to "tune out" the sound as this is a sound that the brain tries to control. When the patient is surrounded by normal environment sounds, they may not be aware of the sound emanating from the devices as the normal environment sounds may cover the sound of the devices. However, the devices should always produce sound.

Changes are slow, incremental and subtle with the goal being for the patient to become comfortable in a busy, noisy world and be able to make the transition to appropriate amplification (hearing aids) if needed. If the transition to hearing aids is made, the patient will no longer need to wear the sound generating devices. There may be periods of time in which the sound sensitivity of the patient may fluctuate, which is normal.

Counseling on Loudness Suppression (LS) Device

The purpose of LS is to limit exposure to uncomfortably loud sounds in sound environments that the user cannot control. Over the course of treatment with the sound generators, the goal is to reduce reliance on LS as the patient's sound tolerance improves. This process is slow and gradual as the patient adjusts to being exposed to healthy and comfortable but louder sounds. For safety, if the patient unexpectedly experiences an uncomfortably loud sound or sound environment, there is an "off toggle" on the device that can be used in the closed mold system to turn off the device, which effectively allows the device to perform as a well-fit, strongly-attenuating earplug. Neither the protective closed mold system nor LS are providing treatment. Rather, these systems reduce exposure to offending sounds by reducing their level. The low-level sound from the sound generators provides the treatment and therefore the sound generators should be used as much as possible each day with one or the other earmold systems.

LS Device

LS device 10 is worn behind the ears and it is custom fit to the patient's ears and hearing. Two different earmolds are used at different times. One earmold system, closed earmold 20, is fashioned like an ear plug and functions as an ear plug when the device is turned off. One purpose of closed ear mold 20 is to reduce the level of all sounds when device 10 is powered off, the same as a traditional earmold. Closed earmold 20 can be used with LS device 10 to form a closed earmold system which provides normal exposure to comfortable sound levels while at the same time limiting exposure to uncomfortably loud sounds.

The second earmold system is an open earmold 30 that is used when the patient is listening to soft and comfortably healthy sound levels when in a controlled, low-level sound environment, such as the patient's home. Under these controlled conditions, the LS is not activated. The purpose of open earmold 30 is to allow the patient to continue to wear LS device 10 at times when the patient would not want or feel the need to wear an earplug. Open earmold 30 can be used with LS device 10 to form an open earmold system which is used when the patient does not anticipate exposure to uncontrolled sound environments.

The closed-mold system is used whenever the patient expects they may be exposed to uncontrolled sound environments, including environments in which the patient currently uses ear plugs. One of the earmold systems (closed or open) should be used as much as possible throughout the day while the patient is awake to allow the patient to receive maximum treatment effects from the SG. Initially, the patient may not wish to use the LS devices 10 for prolonged periods of time if they feel uncomfortable with the earmolds in their ears. In this case, the patient can build up use of the devices 10 each day toward a goal of device usage at least 8 hours a day, and then to the recommended goal of device usage throughout the waking day. Full benefit of the treatment is dependent on prolonged use of the devices on a daily basis.

Each LS device 10 is marked for either the left or the right ear. In order to insert the device into the ear, the LS device shell 50 is slipped behind the top of the ear with tubing 40 hanging down in front of the ear. The soft dome flex tip of earmold should point toward the opening of the ear canal into which it is gently inserted until polytube 40 is flush with the outer ear. In fitting, the patient may need to pull the top of the ear with their hand to allow for easy insertion into the ear canal. It is important not to expose the devices to water or high temperatures or humidity. The devices can be inspected each night and the polytube removed and cleaned to remove debris.

Within 2 weeks after the device fitting, sound generator 60 is activated and baseline outcomes are measured by several means including audiometrics; questionnaires related to hyperacusis, tinnitus, QOL, distress and anxiety; contour categorical loudness as a basis for LS release and to establish presentation level for connected speech test (CST); CST at categories 4 and 6; and device usage. Loudness suppression is released about every 4 weeks with outcome measures being taken about every 8 weeks, dependent on how the patient progresses.

Loudness Suppression (LS) Fitting Protocol

Generally, LS fitting requires established communication between the ear-level devices, the fitting software, and the probe-microphone hearing instrument verification software/hardware system. Prior to LS fitting, the patient should have undergone LS device counseling. General instructions for this evaluation should include a description of the nature of this session, goals for device fitting and verification, and description of the sounds to be heard during the session.

First, the device is connected to the programming computer with communication being established between (1) the fitting software on the computer and the device and (2) the fitting software and software controlling a probe microphone (real-ear) hearing aid verification system. The probe-microphone system is recalibrated according to manufacturer specification before each session.

It is important that prior to this session, the patient has completed LS device counseling. In each session, connectivity is established between the fitting software and the verification system. The following steps are performed on one ear with the first device and then subsequently on the second ear with the second device.

The fitting software is preloaded with patient fitting data from the previous fitting or re-fitting session and the patient is seated in front of the real-ear system. Otoscopy and any necessary cerumen management is completed prior to the session. The probe tube assembly is secured, and the probe tube is positioned such that probe tube is at least 5 mm from the end of the earmold terminus but does not contact the tympanic membrane. A first ear is chosen for fitting and verification.

The first measurement is for the real-ear unaided response (REUR). Measurement is conducted by running a speech signal for leveling as a stimulus to account for the difference between the reference microphone at calibration versus in situ. The stimulus is run for only 1 second without recording and the measurement is stopped once the curve is visualized. The stimulus is then changed on the same curve and the measurement is conducted and recorded to obtain the REUR curve.

Prior to inserting hearing device, the real-ear unaided response is measured using a broadband noise from the verification system as described above. In order to set up the devices, verify that both devices are muted and that the sound generator is off. The earmold is inserted into the patient's ear and sufficient time is allowed for the heat-activated stint to engage and expand.

The second measurement is sound generator (SG) calibration preceded by an estimation of the verification noise floor. Knowledge of the verification system noise floor is essential for interpretation of each of the subsequent measurements. All measurement stimuli must be above the system noise floor at all relevant frequencies and below the loudness tolerances of the patient. To estimate the verification noise floor, a speech stimulus is used to measure the verification noise floor. This measurement is then compared to an estimate of the noise floor in the software as well as KEMAR noise floor.

In order to calibrate the SG, the SG is unmuted, and a white noise stimulus is administered. The curve of the SG calibration noise is then measured and recorded.

The next measurement is to record the real-ear occluded response (REOR), have the patient insert both ear molds, with the non-test ear functioning as an earplug, in order to avoid overstimulation via the test stimulus. Mute the SG and amplifier of each hearing device and measure the REOR using a broadband or white noise from the verification system speakers.

In order to evaluate noise floor, REUR, and REOR responses, compare the data to reference data that is available in the fitting software. If there are marked discrepancies then troubleshooting, including evaluation of the probe tube placement and device function, can be performed.

Unity gain, combined with LS, allows normal exposure to soft and comfortably loud input sounds and loudness suppression of input sounds that exceed patient tolerance. In order to establish unity gain and verify real-ear aided response (REAR), the patient is instructed on the sounds to be heard. The SG is muted, and the microphones/amplification are unmuted. Real-ear aided response (REAR) is measured to broadband or white noise stimulus that is presented at a suitable level. In general, loudness category levels 1-4 are assessed with the patient making a judgment as to how loud the sound is as it increases. Each increase is by 2 dB. While broadband noise is playing, the gain-frequency response is adjusted so that the REAR matches the REUR curve as needed to achieve unity gain. This gain effectively overcomes the earplug attenuation associated with the occluding ear mold and results in real-ear insertion gain (REIG) that is 0 dB across frequency.

In order to adjust LS, the output limit in the software is initially set to the required level (e.g. 65 dB) for high inputs (e.g. 90 dB) on the basis of LDL or loudness category 6 categorical judgments. To verify an acceptable setting, a relatively high-level speech stimulus from the verification device is first administered followed by a slow release (decrease) output limiting from a low output limit until the patient reports that the loudness of the speech is a category 6 ("loud, but ok"). The response curve for high level speech is measured to verify that hearing output does not exceed the previously set output limit.

The LS compression thresholds for each subject are set at levels based on their individual, frequency-specific, loudness discomfort levels, to limit higher level sound exposures similarly to exposures limited by his/her sound attenuators pretreatment. The LS compression thresholds are increased systematically (based on treatment-related improvements in each subject's loudness judgments measured periodically) to reduce the effect of compression, thereby gradually increasing exposure to higher-level healthy sounds. Thus, as the treatment effect is realized, higher LS compression thresholds transition the patient to normal (compression-free) hearing, essentially weaning the patient off of the pretreatment sound attenuators and preparing the patient for any needed amplification as a result of comorbid hearing loss (if it exists).

Sound Generator (SG) Fitting Protocol

Generally, SG fitting requires established communication between the ear-level devices, the fitting software, and the probe-microphone hearing instrument verification software/hardware system. Prior to SG fitting, the patient should have undergone SG device counseling. The SG should be set to a very low level and shaped according to the desired frequency response. The SG should be enabled and gradually increased by about 2 dB. For each increase, the patient should provide categorical loudness judgments and the SG level should be set to a level corresponding to the category comfortable, but soft. The patient should be reminded that their perception of the sound may fade with time, so it's important for the sound to be audible and not too soft (Contour Test Category 3—"comfortable, soft") when initially setting the SG level.

First, the device is connected to the programming computer with communication being established between (1) the fitting software on the computer and the device and (2) the fitting software and software controlling a probe microphone (real-ear) hearing aid verification system. The probe-microphone system is recalibrated according to manufacturer specification before each session.

It is important that prior to this session, the patient has completed LS device counseling. In each session, connectivity is established between the fitting software and the verification system. The fitting software is preloaded with patient fitting data from the previous fitting or re-fitting session and the patient is seated in front of the real-ear system. Otoscopy and any necessary cerumen management is completed prior to the session. The probe tube assembly is secured, and the probe tube is positioned such that probe tube is at least 5 mm from the end of the earmold terminus but does not contact the tympanic membrane. A first ear is chosen for fitting and verification. Knowledge of the verification system noise floor is essential for interpretation of each of the subsequent measurements. All measurement stimuli must be above the system noise floor at all relevant frequencies and below the loudness tolerances of the patient.

In order to set up the devices, both devices are muted, and the sound generator is off. The earmold is inserted into the patient's ear and sufficient time is allowed for the heat-activated stint to engage and expand. The device to be set is unmuted and placed in the first ear.

In order to set the SG level of the first device, the patient is first instructed to establish the level at which the SG is perceived to be comfortable but soft according to the Contour Loudness Test (Category 3). The SG level is then varied by about +/−2 dB to establish loudness categories 1 to 4. The patient is instructed that the perception of the sound will fade with time, so it is important for the sound to be audible and not too soft during this step. The SG/therapy noise is adjusted to have the desired spectral shape and the SG is activated at a low level. Categorical loudness judgments are obtained and the real-ear sound generator (RESG) level is measured to quantify SG output. These steps are repeated for the second device and both devices are balanced by activating both devices simultaneously which comprises muting the SG and turning on both devices then turning on the SG in both devices and asking the patient if one device is louder than the other. If the SG in one device is louder than the other device, then the two devices are adjusted to have equal loudness.

Figure 12:
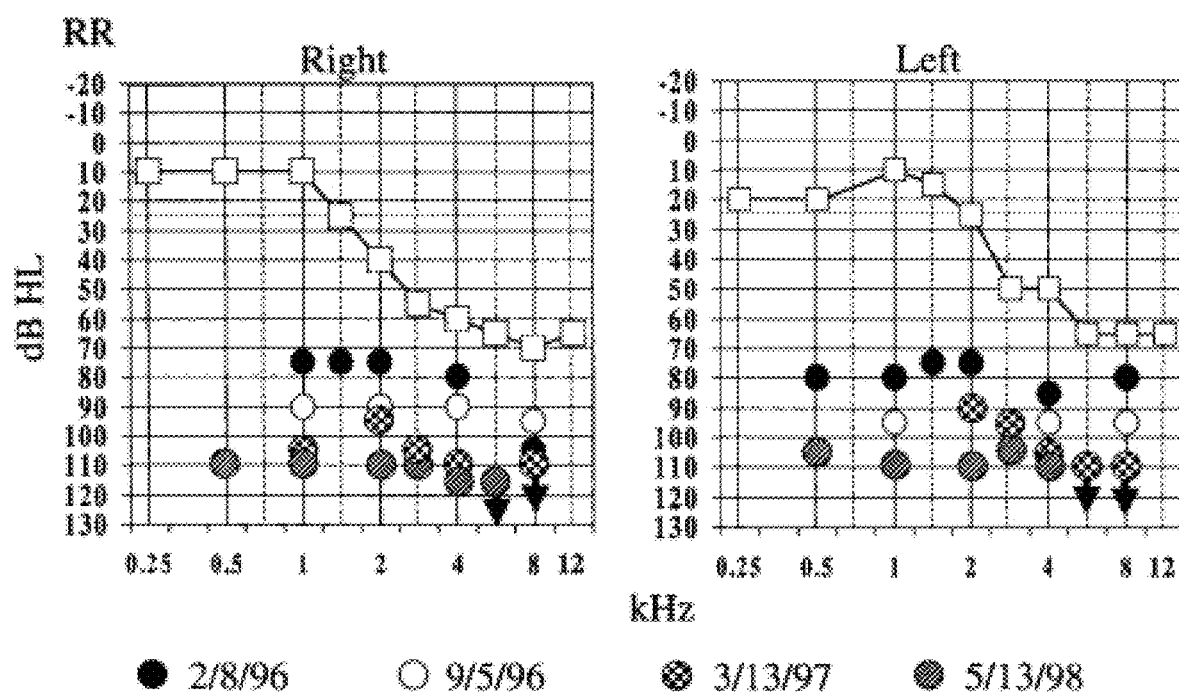
FIG. 12 is a series of graphs depicting audiograms taken of a patient suffering from tinnitus and hyperacusis. As shown in the graphs, the patient's LDLs were low at the beginning of treatment and then improved over the course of treatment. (Formby and Gold 2002).

Many people who have hyperacusis also have tinnitus, a condition in which people hear sounds within their ears or in their head when there is no external sound. The treatment described herein also works for many individuals with tinnitus after the hyperacusis subsides. FIG. 12 illustrates an example of a patient who had tinnitus and hyperacusis. As noted in the image, the patient's LDLs were low at the beginning of the treatment and then improved over the course of treatment.

While the invention is described with respect to hyperacusis, the system and method can be applied to other patient groups including those patients having autism who have a hypersensitivity to sound as well as hunters who require situational awareness as the loudness suppression can protect the individual from loud sounds.

Prophetic Example

A patient presents with primary hyperacusis and is evaluated by administration of audiometric evaluation as well as custom questionnaires. The audiometric evaluation includes determining both unoccluded and occluded (using the patient's current earplugs) thresholds, loudness determinations, and speech determinations. Tone decay is also determined. Ear canal impressions are made for ordering custom closed and open earmolds.

In the first treatment visit, counseling (both LS and SG) are provided to the patient as enumerated in the counseling protocols. The LS device is fit to the patient using real-ear measures with the unity gain (UG) frequency response being achieved by adjusting the REAG to compensate for the REOG, thereby reproducing REUG (offsetting the insertion loss) for the closed mold LS condition as detailed in the LS fitting protocol. The LS device with UG will replace the patient's current sound attenuation (earplugs/muffs). The LS device offers enhanced audibility and a larger dynamic range. Initial LS threshold Initial LS compression threshold parameters are determined on the basis of loudness judgments for "loud but ok" (Contour Category 6) measured bilaterally from 250 to 8000 Hz, with SPL values verified via hearing instrument test measures (Audioscan VF-2). Counseling on device use, care, and expectations will be provided. LS devices may be worn for between 2 weeks to about one month before activation of the sound generators (SGs). Counseling for SG is provided to the patient prior to SG fitting according to protocol provided. Sound generators are activated with the SG set to a very low level and shaped according to the desired frequency response. The SG should be enabled and gradually increased by about 2 dB. For each increase, the patient should provide categorical loudness judgments and the SG level should be set to a level corresponding to the category comfortable, but soft. The patient should be reminded that their perception of the sound may fade with time, so it's important for the sound to be audible and not too soft (Category 3—"comfortable, soft") when initially setting the SG level. The patient is encouraged to wear the open earmold when in a safe sound controlled environment and the closed earmold when in an environment in which they may encounter unexpected high-level sounds with usage of both earmolds totaling at least 8 hours per day or as much as can be tolerated throughout the day.

The patient is monitored at regular intervals for adjustments to be made to the loudness suppression as the dynamic range is expanded with the goal being that as the treatment effect is realized, higher LS compression thresholds transition the patient to normal (compression-free) hearing, essentially weaning the patient off of the pretreatment sound attenuators and preparing the patient for any needed amplification as a result of comorbid hearing loss (if it exists).

CONCLUSION

The inventors have developed a patient-specific system and method of expanding the dynamic range in patients having a hypersensitivity to ordinary sound which utilizes a device having sound attenuation in conjunction with loudness suppression and a sound generator in conjunction with counseling. Expanding the dynamic range can be beneficial for any SNHL plus amplification.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between. Now that the invention has been described.

What is claimed is:

1. A method of diminishing hypersensitivity to sound in a patient in need thereof comprising:
    providing a pair of in-ear hearing devices, each comprising:
        two interchangeable earmolds wherein one earmold is closed and another earmold is open wherein the earmolds conform substantially to the diameter and geometry of the patient's ear;
        a behind the ear shell connected to one of the earmolds by tubing;
        a receiver component, a sound generator component, at least one microphone and a signal processing component containing an amplifier all contained within the shell; and
        fitting software in electronic communication with the signal processing component, the fitting software configured to execute instructions from the signal processing component to control adjustment of noise generation and loudness suppression compression in the hearing device;
    counseling the patient on loudness suppression and the sound generator after providing the in-ear hearing devices;
    adjusting loudness compression thresholds based on a patient's frequency-specific loudness discomfort levels after counseling the patient on loudness suppression and the sound generator;
    fitting the sound generator to the patient by configuring the sound generator to a set level corresponding to a patient-specific soft loudness judgement after adjusting the loudness compression thresholds; and
    systematically increasing the loudness compression thresholds in subsequent sessions with an audiologist to transition the patient to normal hearing.

2. The method of claim 1, wherein the patient wears both devices as long as can be tolerated in the waking day.

3. The method of claim 1, wherein the open earmold is swapped for the closed mold and is worn by the patient when in a controlled sound environment where no unexpected sounds are present.

4. The method of claim 1, wherein the closed mold is worn by the patient when the patient expects to be exposed to an uncontrolled sound environment.

5. A method of treating hyperacusis in a patient in need thereof comprising:
    providing a pair of in-ear hearing device, each device comprising:
        two interchangeable earmolds wherein one earmold is a closed mold and the other earmold is an open mold which conform substantially to the diameter and geometry of the patient's ear;
        tubing connecting one of the two interchangeable earmolds to a behind the ear shell;
        a signal processor containing an amplifier, at least one microphone, a receiver, and a sound generator electrically connected and contained within the behind the ear shell;
        fitting software in electronic communication with the signal processing component, the fitting software configured to execute instructions from the signal processing component to control adjustment of noise generation and loudness suppression compression in the hearing device;

counseling the patient on the sound generator after providing the in-ear hearing devices;

counseling the patient on the hearing devices after counseling the patient on the sound generator;

connecting the devices to a programming computer after counseling the patient on the hearing devices;

measuring a real ear unaided response (REUR) after connecting the devices to the programming computer;

fitting the hearing devices with the closed molds to each ear of the patient after measuring the REUR comprising:

positioning each hearing device so that the earmold of the hearing device is inserted into one of the patient's ears wherein one ear is a test ear and the other ear is a non-test ear;

estimating a verification noise floor after positioning each hearing device in each of the patient's ears;

measuring real ear occluded response (REOR) by muting the sound generator, amplifier and microphones and administering a broadband or white noise from verification system speakers in the test ear after estimating the verification noise floor;

measuring real ear aided response (REAR) after measuring the REOR;

adjusting a gain-frequency response so that the REAR matches the REUR curve to achieve unity gain and result in real-ear insertion gain (REIG) that is 0 dB across frequency after measuring REAR;

adjusting loudness compression thresholds based on a patient's frequency-specific loudness discomfort levels after adjusting the gain-frequency response; and repeating above steps for the other device in the non-test ear;

fitting the sound generator to the patient by configuring the sound generator to a set level corresponding to a patient-specific soft loudness judgement after fitting the hearing devices comprising:

inserting the one hearing device into each of the test and non-test ears of the patient;

activating the sound generator of the hearing device in the test ear of the patient to emit a low-level broadband noise after inserting the hearing device;

establishing a level with the patient where the noise is perceived to be comfortable but soft according to the Contour Loudness Test Category 3 after activating the sound generator;

varying loudness of the noise and obtaining categorical loudness judgments on the noise from the patient after establishing the level where the noise is comfortable but soft;

measuring real-ear sound generator (RESG) level to quantify SG output after varying the loudness of the noise and obtaining the categorical loudness judgments from the patient;

repeating above steps for the hearing device in the non-test ear; and balancing both devices after the above steps are conducted on both the test and non-test ears of the patient; and systematically increasing the loudness compression thresholds in subsequent sessions with an audiologist to transition the patient to normal hearing.

6. The method of claim 5, further comprising administering audiometric testing to the patient prior to providing the hearing device to the patient.

7. The method of claim 5, further comprising muting the receiver and amplifier and the at least one microphone of both hearing devices with the sound generator off prior to inserting the hearing devices into the patient's ears.

8. The method of claim 5, wherein the sound generator is calibrated after estimating the noise floor by unmuting the sound generator and administering a white noise stimulus in the test ear.

9. The method of claim 5, further comprising comparing data from REOR, REUR and noise floor to reference data in the fitting software prior to the fitting the sound generator.

10. The method of claim 5, wherein the REAR is measured by the steps comprising:

muting the sound generator;

unmuting the receiver and amplifier and microphones after muting the sound generator;

administering a broadband or white noise stimulus to the test ear after unmuting the receiver;

having the patient categorize loudness of the stimulus after administering the broadband or white noise; and subsequently increasing a frequency of the stimulus at intervals until the patient reports loudness category 6 categorical judgment.

11. The method of claim 5, wherein the patient wears both devices for at least 8 hours per waking day.

12. The method of claim 5, wherein the open earmold is swapped for the closed mold and is worn by the patient when in a controlled sound environment where no unexpected sounds are present.

13. The method of claim 5, wherein all measurement stimuli are emitted at frequencies above the noise floor.

14. The method of claim 5, wherein the both devices are balanced by activating the both devices simultaneously and adjusting each device to have equal loudness.

15. The method of claim 5, wherein loudness suppression is released about every 4 weeks.

16. The method of claim 5, wherein the closed mold is worn by the patient when the patient expects to be exposed to an uncontrolled sound environment.

17. A system for use in treatment of hyperacusis in a patent in need thereof comprising:

a hearing device comprising:

two interchangeable earmolds wherein one earmold is a closed mold and the other earmold is an open mold which conform substantially to the diameter and geometry of the patient's ear;

tubing connecting one of the two interchangeable earmolds to a behind the ear shell; and a signal processor containing an amplifier, at least one microphone, a receiver, and a sound generator electrically connected and contained within the behind the ear shell;

fitting software in electronic communication with the signal processor, the fitting software configured to execute instructions from the signal processor to control adjustment of noise generation and loudness suppression in the hearing device;

verification software in electronic communication with the fitting software wherein the verification software is configured to transmit reference data to an external computing device for comparison with patient data; and a counseling protocol wherein the counseling protocol provides counseling for both the sound generator and the loudness suppression.

18. The system of claim 17, wherein the hearing devices are inserted into the patient's ears and loudness compression thresholds are adjusted based on a patient's frequency-specific loudness discomfort levels.

19. The system of claim 18, wherein the sound generator is fitted to the patient by configuring the sound generator to a set level corresponding to a patient-specific soft loudness judgement.

20. The system of claim 19, wherein the loudness compression thresholds are systematically increased in subsequent sessions with an audiologist to transition the patient to normal hearing.

* * * * *